US012337127B2

(12) United States Patent
Harding et al.

(10) Patent No.: US 12,337,127 B2
(45) Date of Patent: Jun. 24, 2025

(54) PROVIDING RESISTANCE TO SEPARATION OF A CATHETER ADAPTER AND A NEEDLE HUB

(71) Applicant: Becton, Dickinson and Company, Franklin Lakes, NJ (US)

(72) Inventors: Weston F. Harding, Lehi, UT (US); Ralph L. Sonderegger, Farmington, UT (US); Joseph Spataro, Cottonwood Heights, UT (US); S. Ray Isaacson, Layton, UT (US); Shaun Staley, Murray, UT (US); Curtis H. Blanchard, Riverton, UT (US); Jonathan Karl Burkholz, Salt Lake City, UT (US); Bin Wang, Sandy, UT (US); Olivia Hu, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 51 days.

(21) Appl. No.: 16/902,963

(22) Filed: Jun. 16, 2020

(65) Prior Publication Data
US 2020/0398030 A1 Dec. 24, 2020

Related U.S. Application Data

(60) Provisional application No. 62/864,292, filed on Jun. 20, 2019.

(51) Int. Cl.
*A61M 25/06* (2006.01)
*A61M 39/10* (2006.01)

(52) U.S. Cl.
CPC .... *A61M 25/0637* (2013.01); *A61M 25/0606* (2013.01); *A61M 25/0693* (2013.01); *A61M 39/10* (2013.01); *A61M 2039/1077* (2013.01)

(58) Field of Classification Search
CPC .......... A61M 25/0637; A61M 25/0606; A61M 39/10; A61M 2039/1077; A61M 39/1011;
(Continued)

(56) References Cited

U.S. PATENT DOCUMENTS

| 3,906,946 A | * | 9/1975 | Nordstrom | ............ | A61M 5/158 |
| | | | | | 604/177 |
| 4,013,080 A | * | 3/1977 | Froning | ................ | A61M 39/10 |
| | | | | | 604/165.01 |

(Continued)

FOREIGN PATENT DOCUMENTS

| AT | 206627 T | 10/2001 |
| AU | 687659 B2 | 2/1998 |

(Continued)

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

A catheter system may include a catheter adapter and a wing extending outwardly from the catheter adapter. The wing may include a groove or slot. The catheter system may include a needle hub and a paddle extending outwardly from the needle hub. The paddle may include an extension disposed within the groove or the slot to reduce axial movement between the catheter adapter and the needle hub, which may be advantageous during insertion of the catheter system into a patient. The extension may be removable from the groove or the slot to allow axial movement between the catheter adapter and the needle hub during removal of the needle hub from the catheter adapter, for example. The paddle and/or the wing may include a shape to reduce axial movement between the catheter adapter and the needle hub, which may also be advantageous during insertion of the catheter system.

8 Claims, 45 Drawing Sheets

(58) Field of Classification Search
CPC ...... A61M 25/0693; A61M 2005/1586; A61M 25/0097; A61M 5/14; A61M 5/158; A61M 39/12; A61M 2005/1587
See application file for complete search history.

(56) References Cited

U.S. PATENT DOCUMENTS

| | | | | |
|---|---|---|---|---|
| 5,498,241 | A * | 3/1996 | Fabozzi | A61M 25/0631 604/177 |
| 5,697,914 | A * | 12/1997 | Brimhall | A61M 25/0637 604/177 |
| 5,935,110 | A | 8/1999 | Brimhall | |
| 6,613,014 | B1 * | 9/2003 | Chi | A61M 25/0097 604/93.01 |
| 6,942,647 | B2 | 9/2005 | Nickels | |
| 2001/0041871 | A1 | 11/2001 | Brimhall | |
| 2007/0016148 | A1 | 1/2007 | Iwase et al. | |
| 2014/0074047 | A1 | 3/2014 | Calderon et al. | |
| 2017/0120009 | A1 * | 5/2017 | Garrison | A61M 25/0637 |
| 2017/0120010 | A1 * | 5/2017 | Burkholz | A61M 25/0631 |
| 2017/0120011 | A1 * | 5/2017 | Burkholz | A61M 25/0637 |
| 2017/0120012 | A1 * | 5/2017 | Sonderegger | A61M 25/0637 |
| 2017/0120013 | A1 * | 5/2017 | Peterson | F16L 35/00 |
| 2017/0120014 | A1 * | 5/2017 | Harding | A61M 25/065 |
| 2017/0120015 | A1 * | 5/2017 | Burkholz | A61M 25/0637 |
| 2017/0120016 | A1 * | 5/2017 | Burkholz | A61M 25/0693 |
| 2017/0274182 | A1 * | 9/2017 | O'Bryan | A61M 25/0631 |
| 2018/0318557 | A1 * | 11/2018 | Burkholz | A61M 39/10 |
| 2019/0209812 | A1 * | 7/2019 | Burkholz | A61M 25/0606 |
| 2020/0261701 | A1 | 8/2020 | O'Bryan | |

FOREIGN PATENT DOCUMENTS

| | | |
|---|---|---|
| AU | 2016346887 A1 | 5/2018 |
| AU | 2017240482 A1 | 10/2018 |
| AU | 2019204246 A1 | 7/2019 |
| BR | 112018069752 A2 | 2/2019 |
| CA | 2168713 A1 | 9/1996 |
| CA | 3002665 A1 | 5/2017 |
| CA | 3018737 A1 | 10/2017 |
| CN | 102716541 | 10/2012 |
| CN | 102716541 A * | 10/2012 |
| CN | 106620941 A | 5/2017 |
| CN | 206652048 U | 11/2017 |
| CN | 109069802 A | 12/2018 |
| CN | 213251964 U | 5/2021 |
| DE | 69523171 T2 | 6/2002 |
| DE | 69628366 T2 | 3/2004 |
| EP | 0732120 | 9/1996 |
| EP | 0796117 A1 | 9/1997 |
| EP | 2332611 A1 | 6/2011 |
| EP | 3368125 A1 | 9/2018 |
| EP | 3436126 A2 | 2/2019 |
| EP | 3718592 A1 | 10/2020 |
| ES | 2166408 T3 | 4/2002 |
| ES | 2200035 T3 | 3/2004 |
| JP | 02004384 A | 1/1990 |
| JP | H05329210 A | 12/1993 |
| JP | H08257129 A | 10/1996 |
| JP | 2000088120 A | 3/2000 |
| JP | 3078904 U | 7/2001 |
| JP | 2001259030 A | 9/2001 |
| JP | 2018531760 A | 11/2018 |
| JP | 2018532508 A | 11/2018 |
| JP | 2019509849 A | 4/2019 |
| JP | 2020121173 A | 8/2020 |
| SG | 11201802994 T | 5/2018 |
| SG | 11201808309 T | 10/2018 |
| WO | 9617639 A1 | 6/1996 |
| WO | 2008024440 A1 | 2/2008 |
| WO | 2017074682 A1 | 5/2017 |
| WO | 2017172383 A2 | 10/2017 |

\* cited by examiner

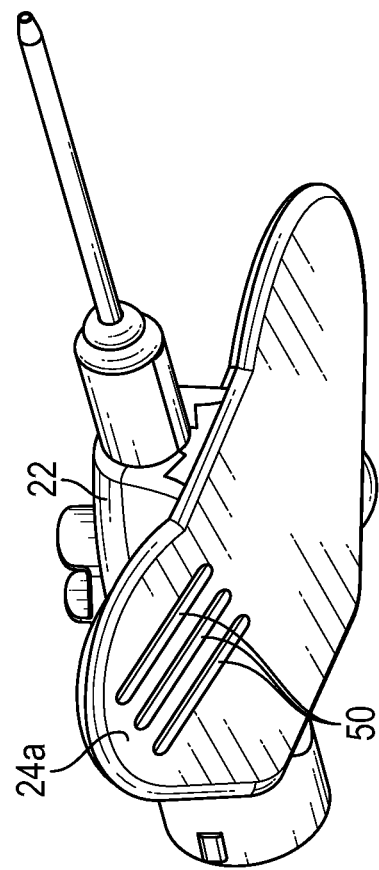
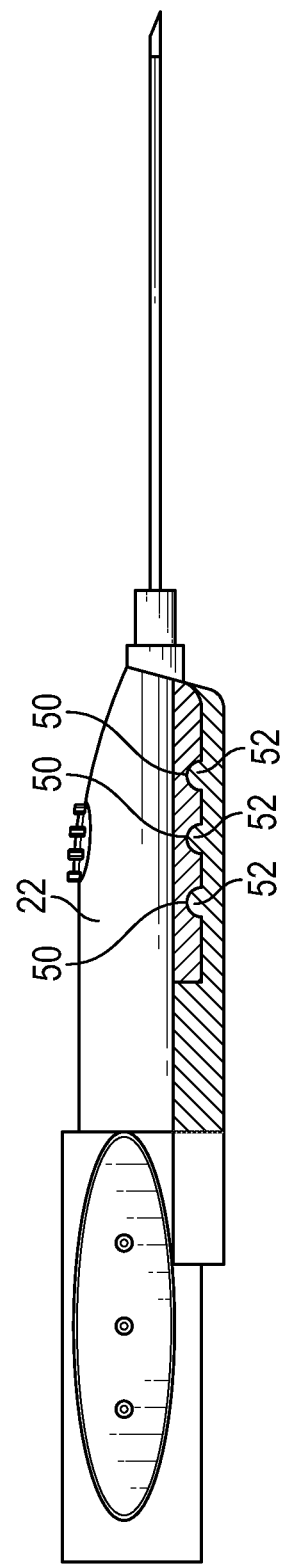
FIG. 4C
FIG. 4D

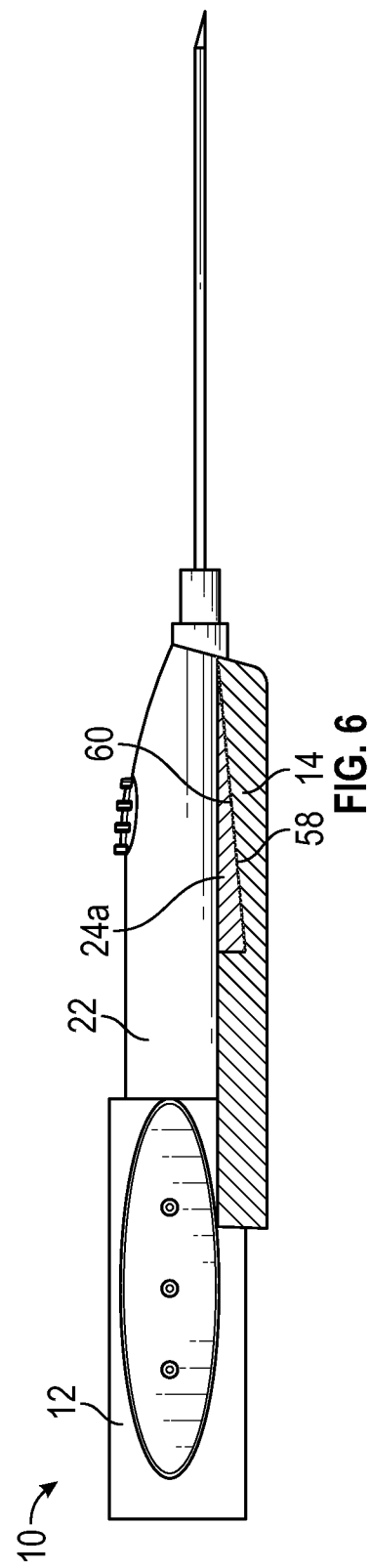

PROVIDING RESISTANCE TO SEPARATION OF A CATHETER ADAPTER AND A NEEDLE HUB

RELATED APPLICATIONS

This application claims the benefit of U.S. Provisional Patent Application No. 62/864,292, filed on Jun. 20, 2019, and entitled PROVIDING RESISTANCE TO SEPARATION OF CATHETER ADAPTER AND A NEEDLE HUB which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intranvenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over an introducer needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient. Once placement of the needle within the vasculature has been confirmed, the user may temporarily occlude flow in the vasculature and withdraw the needle, leaving the intravenous catheter in place for future blood withdrawal and/or fluid infusion.

In order to verify proper placement of the introducer needle and/or the intravenous catheter in the vasculature, a user generally confirms that there is flashback of blood, which may be visible to the user. As an example, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the PIVC. Accordingly, where the PIVC is at least partially transparent, the user may visualize a small amount of blood "flashback" and thereby confirm placement of the PIVC within the vasculature. Presence of a vasculature entrance indicator, such as flashback, may facilitate successful placement of PIVCs.

The subject matter claimed herein is not limited to embodiments that solve any disadvantages or that operate only in environments such as those described above. Rather, this background is only provided to illustrate one example technology area where some implementations described herein may be practiced.

SUMMARY

In some embodiments, a catheter system may include a catheter adapter, which may include a proximal end, a distal end, and a lumen extending through the proximal end and the distal end. In some embodiments, a wing may extend outwardly from the catheter adapter. In some embodiments, the wing may include a groove or slot. In some embodiments, a catheter may extend distally from the catheter adapter. In some embodiments, the catheter system may include a needle hub.

In some embodiments, a paddle may extend outwardly from the needle hub. In some embodiments, the paddle may include an extension, which may include a protrusion. In some embodiments, the extension may be disposed within the groove or the slot to reduce axial movement between the catheter adapter and the needle hub. In some embodiments, the catheter system may include a cannula, which may extend through the catheter adapter and the catheter. In some embodiments, the cannula may include a proximal end and a distal end. In some embodiments, the proximal end of the cannula may be secured within the needle hub.

In some embodiments, the catheter system may include one or more features configured to reduce axial movement between the catheter adapter and the needle hub, which may be advantageous during insertion of the catheter system into a patient. For example, in some embodiments, a bottom of the wing may be smooth. In some embodiments, the extension may include a ball shape and the wing may include a socket that receives the ball shape. In some embodiments, the groove or the slot may be generally perpendicular to a longitudinal axis of the catheter system, and the extension may be configured to move laterally within the groove or the slot but not axially.

In some embodiments, the extension may include a rib. In some embodiments, the wing may include a groove. In some embodiments, the groove may be elongated to generally match a shape of the rib. In some embodiments, the extension is part of a chevron pattern surface, and/or the wing may include a corresponding chevron pattern that includes the groove.

In some embodiments, the extension may be removable from the groove or the slot to allow axial movement between the catheter adapter and the needle hub during removal of the needle hub from the catheter adapter, for example. In some embodiments, the extension may be removable from the groove or the slot in response to force applied by the user. In some embodiments, the wing may be constructed of a flexible material such that the wing may be pulled away from the paddle to remove the extension from the groove or the slot.

In some embodiments, the paddle may include a shape to reduce distal movement of the catheter adapter with respect to the needle hub. In some embodiments, the shape may include a rough texture. In some embodiments, a proximal portion of the paddle may include the rough texture, and/or a distal portion of the paddle may be smooth. In some embodiments, a portion of the paddle may sit underneath the wing. In some embodiments, the shape may include an arm configured to move independently of the portion of the paddle that sits underneath the wing. In some embodiments, in response to the arm being in a first position, the arm may contact a distal end of the wing and reduce distal movement of the wing. In some embodiments, in response to the arm being in a second position, the arm may be disposed below the wing and the wing may be configured to move distally.

In some embodiments, the shape may include a raised distal edge configured to reduce distal movement of the wing. In some embodiments, the paddle may include a raised proximal end. In some embodiments, an edge of the paddle between the raised distal edge, and the raised proximal edge may not be raised.

In some embodiments, the wing may include a recess, and the shape may include a cantilever element movable between a first position within the recess and a second position outside of the recess. In some embodiments, the shape may include a bend forming an upper portion and a lower portion of the paddle, wherein the wing is disposed between the upper portion and the lower portion of the paddle, wherein in response to pinching the upper portion and the lower portion together, movement of the wing is reduced with respect to the paddle.

In some embodiments, the wing may be a first wing. In some embodiments, the catheter system may include a second wing, which may extend outwardly from the catheter adapter. In some embodiments, the second wing may be movable between an up position and a down position. In some embodiments, the second wing may be smaller than the first wing. In some embodiments, the second wing may include a protrusion.

In some embodiments, the paddle may include a groove. In some embodiments, in response to the second wing being disposed in the down position, the protrusion may be disposed in the groove. In some embodiments, in response to the second wing being disposed in the up position, the protrusion may not be disposed within the groove.

In some embodiments, a distal end of the paddle may include a concave curved surface. In some embodiments, the concave curved surface may face distally. In some embodiments, a side of the catheter adapter may include another concave curved surface. In some embodiments, the concave curved surface and the other concave curved surface may be configured to be gripped in a ported grip. In some embodiments, the catheter adapter may include a protrusion configured to contact the paddle and prevent rotation of the needle hub with respect to the catheter adapter. In some embodiments, the paddle may include a groove, and the catheter adapter may include a rib slidable within the groove, which may facilitate alignment between the catheter adapter and the needle hub.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4C is a lower perspective view of the catheter system, according to some embodiments;

FIG. 4D is a cross-sectional view of the catheter system along line 4D-4D of FIG. 4A, according to some embodiments;

FIG. 6 is an alternative cross-sectional view of the catheter system along line 5D-5D of FIG. 5A, according to some embodiments;

DESCRIPTION OF EMBODIMENTS

Figure 1A:
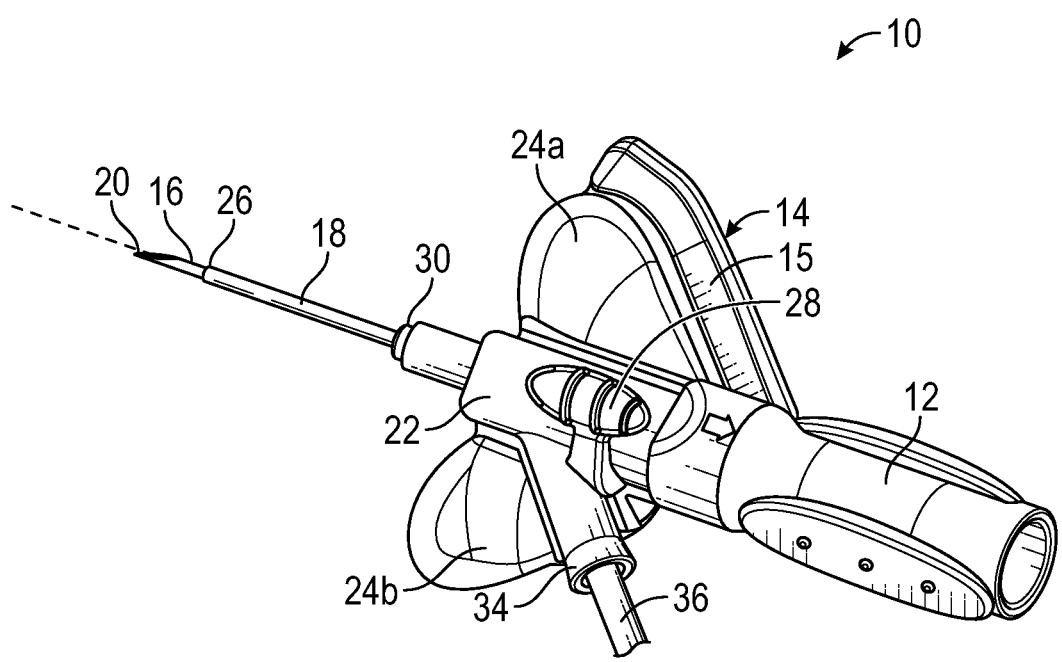
FIG. 1A is an upper perspective view of an example catheter system, illustrating the catheter system in an insertion configuration for insertion into a patient, according to some embodiments.
Figure 1B:
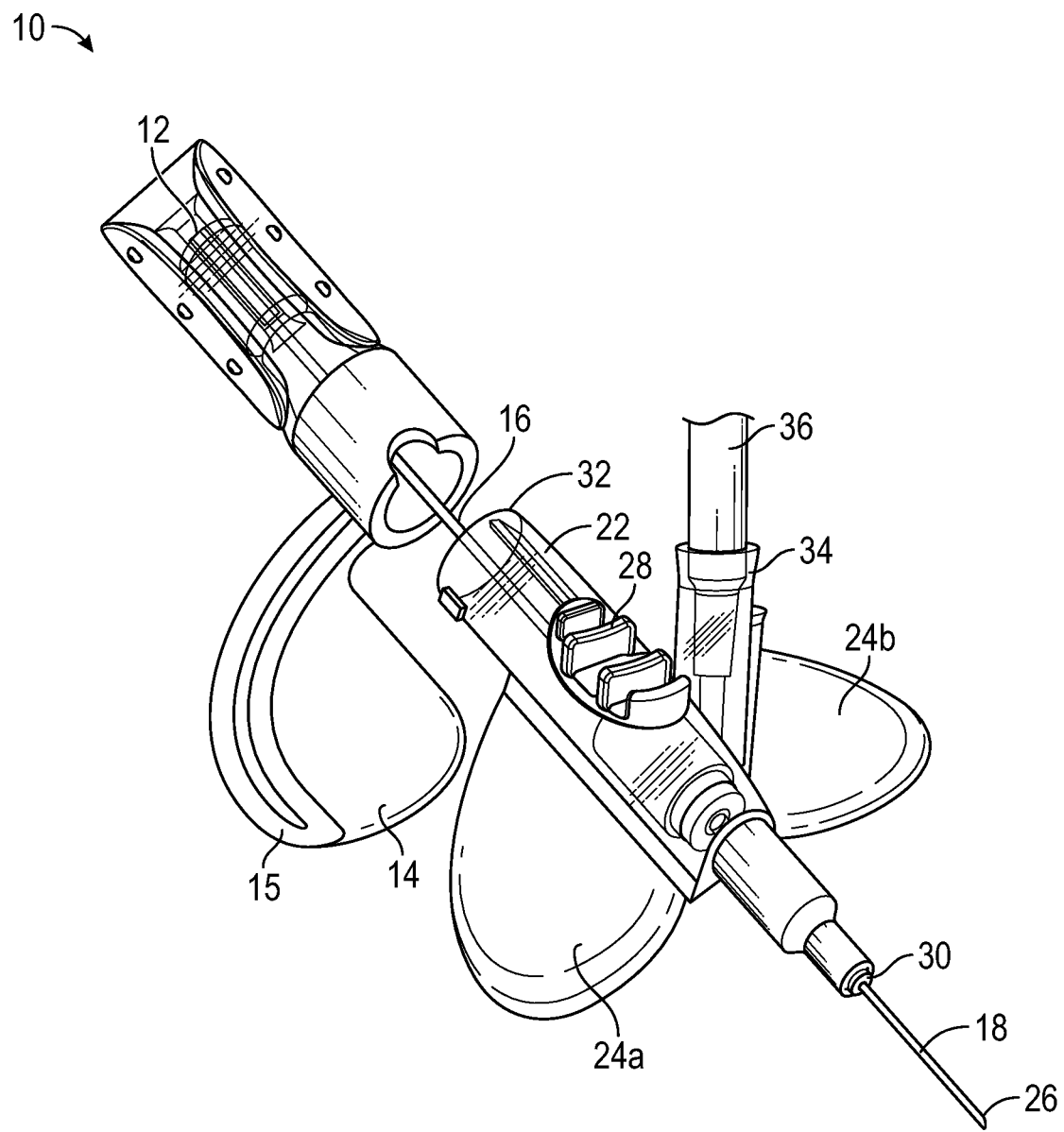
FIG. 1B is an upper perspective view of the catheter system, illustrating an example needle hub removed from an example catheter adapter, according to some embodiments.

Referring now to FIGS. 1A-1B, in some embodiments, a catheter system 10 may include a needle hub 12 and a paddle 14. In some embodiments, the needle hub 12 and the paddle 14 may be a single component and integrally formed. In some embodiments, the needle hub 12 and the paddle 14 may be monolithically formed as a single unit. In some embodiments, the paddle 14 may extend outwardly from the needle hub 12.

In some embodiments, the proximal end of a cannula 16 may be secured within the needle hub 12. In some embodiments, the cannula 16 may include a notch (not illustrated in FIGS. 1A-1C), which may be disposed towards a distal end of the cannula 16 and which may provide primary flashback indicating that a catheter 18 of the catheter system 10 has been properly placed within vasculature of a patient. In some embodiments, the cannula 16 may include an introducer needle having a sharp distal tip 20. In some embodiments, a bevel of the sharp distal tip 20 may face towards a top of the catheter system 10. In some embodiments, flashback may be visible within the needle hub 12.

In some embodiments, the needle hub 12 may be removably coupled to a catheter adapter 22 of the catheter system 10. In some embodiments, one or more wings 24a, 24b may extend outwardly with respect to the catheter adapter 22. As illustrated in FIG. 1A, in some embodiments, a wing 24a may overlap with the paddle 14, which may facilitate the user pinching the wing 24a and the paddle 14 together during insertion of the catheter system 10 into the vasculature of the patient. In some embodiments, during insertion of the catheter system 10, it may be important that the user grip the paddle 14 such that the force the user applies for insertion is transferred directly to the cannula 16. In some embodiments, the paddle 14 may include a ridge 15, which may abut the wing 24a. In some embodiments, the catheter system 10 may not include the wing 24a and/or wing 24b.

In some embodiments, if the user is unsuccessful in penetrating the vasculature with the cannula 16, the user may withdraw the catheter system 10 slightly to redirect a path of the cannula 16 for another attempt at penetrating the vasculature. In some embodiments, during this withdrawal of the catheter system 10, if the user is able to pinch the wing 24a and the paddle 14 together between a thumb and a finger of the user, this may prevent the catheter adapter 22 from separating from the needle hub 12 in response to friction between the catheter system 10 and tissue of the patient during the withdrawal.

Thus, in some embodiments, overlap between the paddle 14 and the wing 24a may facilitate pinching by the user as the catheter system 10, which may inhibit premature separation of the needle hub 12 and the catheter adapter 22. Premature separation of the needle hub 12 and the catheter adapter 22 can result in a distal end 26 of the catheter 18 moving a distance proximal to a bevel of the cannula 16, which may result in catching of the distal end 26 of the catheter 18 on the tissue during a subsequent insertion motion by the user. Catching of the distal end 26 of the catheter 18 on the tissue may be painful for the patient and may deform the distal end 26 of the catheter 18, making entrance into the vasculature difficult or impossible.

In some embodiments, after the catheter 18 has been successfully placed within the vasculature, the cannula 16 may be withdrawn from the catheter 18, and the catheter 18 may be left in place for blood withdrawal, infusion, or another suitable purpose. In some embodiments, in order to withdraw the cannula 16 from the catheter 18, the needle hub 12 may be separated from the catheter adapter 22, and the needle hub 12 may be removed from the catheter system 10 and/or discarded. In some embodiments, the overlap between the paddle 14 and the wing 24a may also facilitate separation of the needle hub 12 and the catheter adapter 22 as the user simply moves his thumb and finger (of a same hand), which were engaged in pinching the needle hub 12 and the catheter adapter 22 during insertion, away from each other. In these embodiments, the finger, such as, for example, an index finger, may move proximally with respect to the thumb.

In some embodiments, during insertion, the thumb may be disposed on a top of the wing 24a, and the finger may be disposed on a bottom of the paddle 14. In some embodiments, the thumb and the finger may maintain these positions on the top of the wing 24a and the bottom of the paddle 14, respectively, in order to separate the needle hub 12 and the catheter adapter 22 after insertion is complete, thus facilitating ease of use of the catheter system 10 for the user. FIG. 1B illustrates the wing 24a separated from the paddle 14, according to some embodiments.

In some embodiments, the catheter adapter 22 may include a push tab 28. In some embodiments, the push tab 28 or another feature coupled to the catheter adapter 22 may align with one or more features of the paddle 14 or markings on the paddle 14 when the catheter system 10 is in the insertion configuration, ready for insertion into the patient. This may provide a visual clue or indication to the user that the catheter adapter 22 and the needle hub 12 is in proper position for insertion and not separated. For example, a distal end of the push tab 28 may align with or be flush with a distal end of the ridge 15. In some embodiments, one or more features of the catheter adapter 22 and/or the catheter system 10 may be described in U.S. patent application Ser. No. 15/969,584, filed May 2, 2018, entitled "INTRAVENOUS CATHETER SYSTEM AND METHODS," which is hereby incorporated by reference in its entirety.

In some embodiments, the catheter adapter 22 may include a distal end 30, a proximal end 32, and a lumen extending through the distal end 30 and the proximal end 32. In some embodiments, the catheter 18 may be secured within the distal end 30 of the catheter adapter 22. In some embodiments, after the needle hub 12 is separated and removed from the catheter adapter 22, a medical device may be coupled to the proximal end 32 of the catheter adapter 22 for infusion and/or blood draw.

In some embodiments, the catheter system 10 may include any suitable catheter adapter 22 and/or needle hub 12. In some embodiments, the catheter adapter 22 may include a side port 34 in fluid communication with the lumen of the catheter adapter. In some embodiments, an extension tube 36 may be integrated within the side port 34 and may be part of an extension set. In some embodiments, the catheter system 10 may include any suitable cannula 16. In some embodiments, the catheter 18 may include a peripheral intravenous catheter ("PIVC"), a midline catheter, a peripherally inserted central catheter ("PICC"), or another suitable catheter.

Figure 1C:
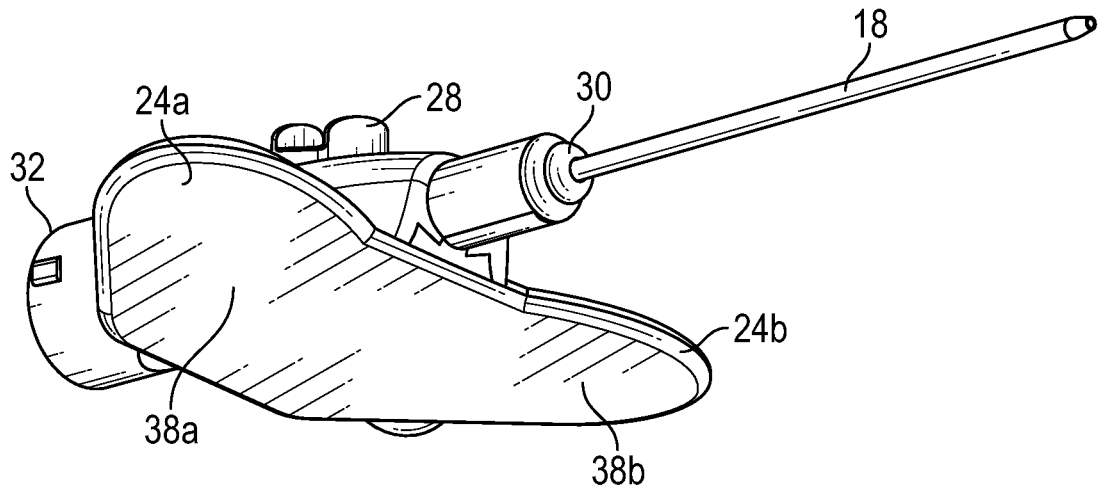
FIG. 1C is a lower perspective view of the catheter system, according to some embodiments.

Referring now to FIG. 1C, in some embodiments, the wing 24a may include a bottom 38a and/or the wing 24b may include a bottom 38b. In some embodiments, the wings 24a, 24b may extend outwardly from the catheter adapter 22. In some embodiments, the wings 24 may be connected to each other or separate from each other. In some embodiments, the bottom 38a and the bottom 38b may form a generally planar surface. In some embodiments, the bottom 38a of the wing 24a and/or a top of the paddle 14 may be smooth such that contact between the wing 24a and the paddle 14 is increased. In some embodiments, with increased contact at the interface between the wing 24a and the paddle 14, friction may be increased between the wing 24a and the paddle 14, which may reduce a likelihood of separation of the wing 24a and the paddle 14 during insertion and/or withdrawal of the catheter system 10 with respect to the vasculature.

In some embodiments, all or a portion of the wing 24a and/or all or a portion of the paddle 14 may not include a lubricant such that friction between the wing 24a and the paddle 14 is increased and a likelihood of separation of the wing 24a and the paddle 14 during insertion of the catheter system 10 into the patient is reduced. In some embodiments, the wing 24a and/or the paddle 14 may be constructed of thermoplastic polyurethane ("TPU") or another suitable material. In some embodiments, the TPU may not include one or more additives, which would otherwise act as lubricants. In some embodiments, the paddle 14 may be more rigid [that] than the wings 24a, 24b. In some embodiments, the paddle 14 may be constructed or TPU or another suitable material.

Referring now to FIGS. 2A-2E, in some embodiments, the catheter system 10 may include a slot 40 and an extension 42 disposed within the slot 40. In some embodiments, the slot 40 may be elongated. In some embodiments, the slot 40 may extend generally perpendicular to a longitudinal axis 44 of the catheter system 10, thus allowing some lateral movement of the extension 42. In some embodiments, a shape and orientation of the slot 40 may prevent the extension 42 (and wing 24a or paddle 14 to which the extension 42 may be attached) from moving axially. In further detail, the shape and the orientation of the slot 40 may prevent the extension 42 parallel to the longitudinal axis 44 and/or in a distal direction or a proximal direction. Thus, in some embodiments, the slot 40 and the extension 42 may reduce a likelihood of separation of the wing 24a and the paddle 14 during insertion and/or withdrawal of the catheter system 10 with respect to the vasculature.

In some embodiments, the extension 42 may extend upwardly from the paddle 14, and the wing 24a may include the slot 40. In some embodiments, the wing 24a may be constructed of a flexible material such that the wing 24a may be pulled or deflected away from the paddle 14 by the user in order to separate the needle hub 12 from the catheter adapter 22 after insertion of the catheter system 10 within the vasculature is complete. In some embodiments, the extension 42 may extend downwardly from the wing 24a, and the paddle 14 may include the slot 40.

Figure 2A:
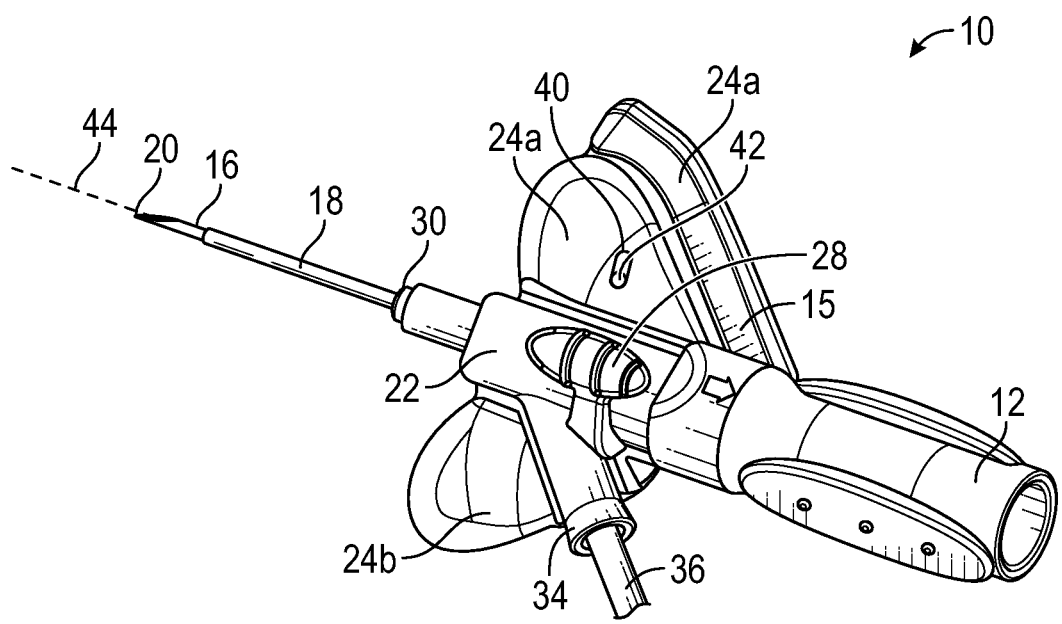
FIG. 2A is an upper perspective view of the catheter system, illustrating an example extension and an example slot, according to some embodiments.
Figure 2B:
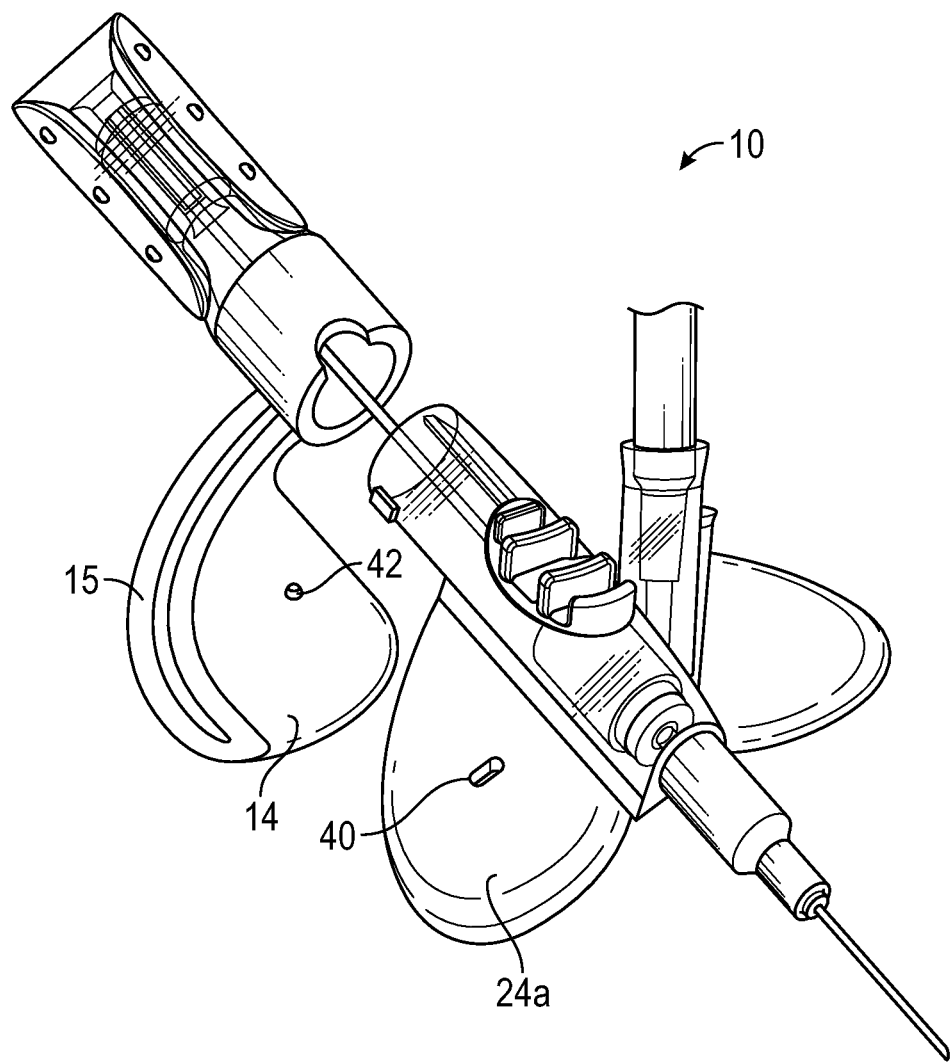
FIG. 2B is an upper perspective view of the catheter system, illustrating the needle hub removed from the catheter adapter, according to some embodiments.
Figure 2C:
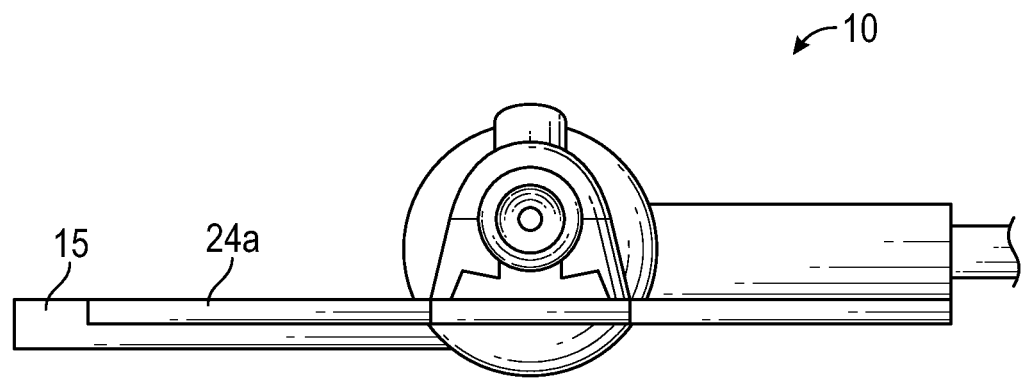
FIG. 2C is a distal end view of the catheter system, according to some embodiments.
Figure 2D:
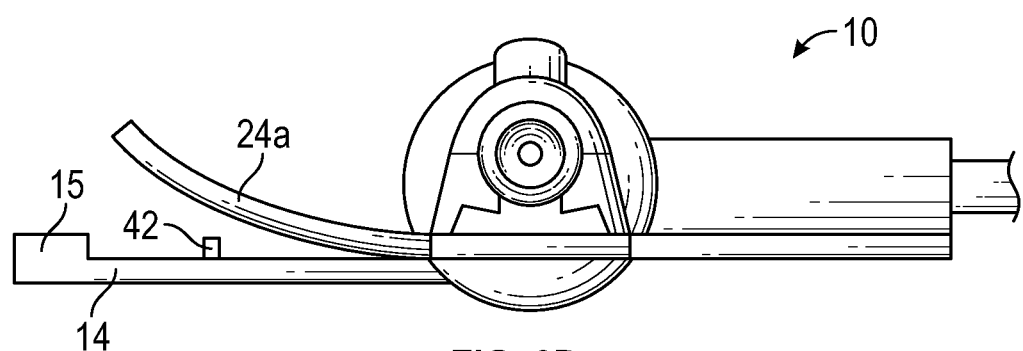
FIG. 2D is another distal end view of the catheter system, illustrating an example wing pulled away from an example paddle, according to some embodiments.
Figure 2E:
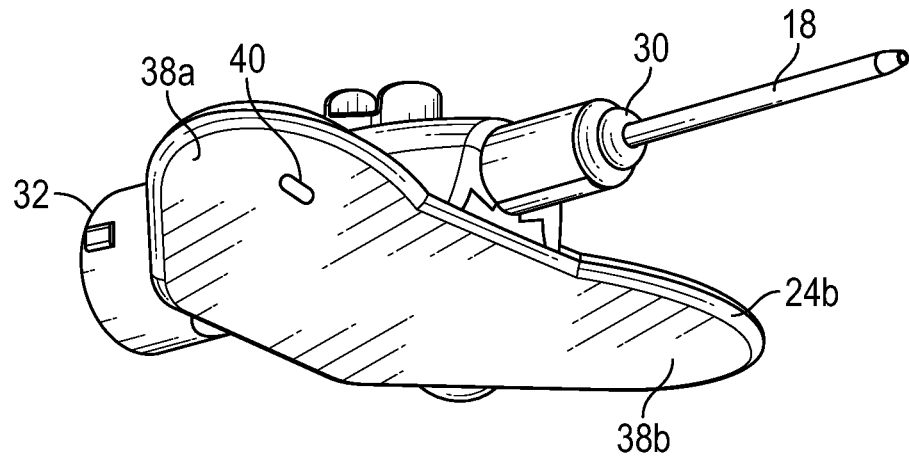
FIG. 2E is a lower perspective view of the catheter system, according to some embodiments.
Figure 3A:
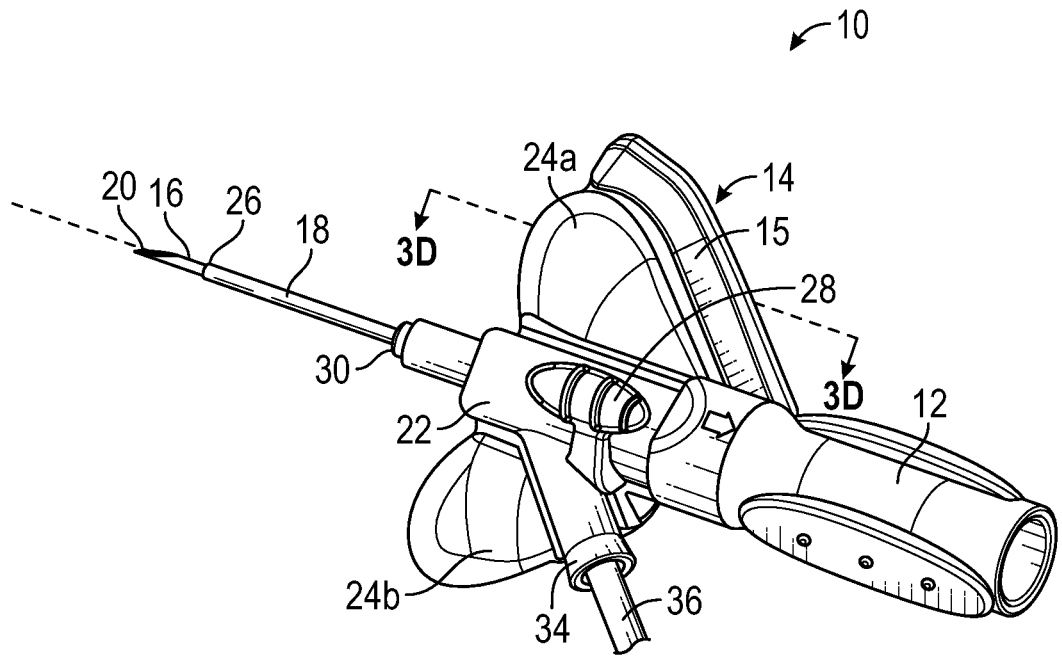
FIG. 3A and FIG. 3E are each an upper perspective view of the catheter system, according to some embodiments.
Figure 3B:
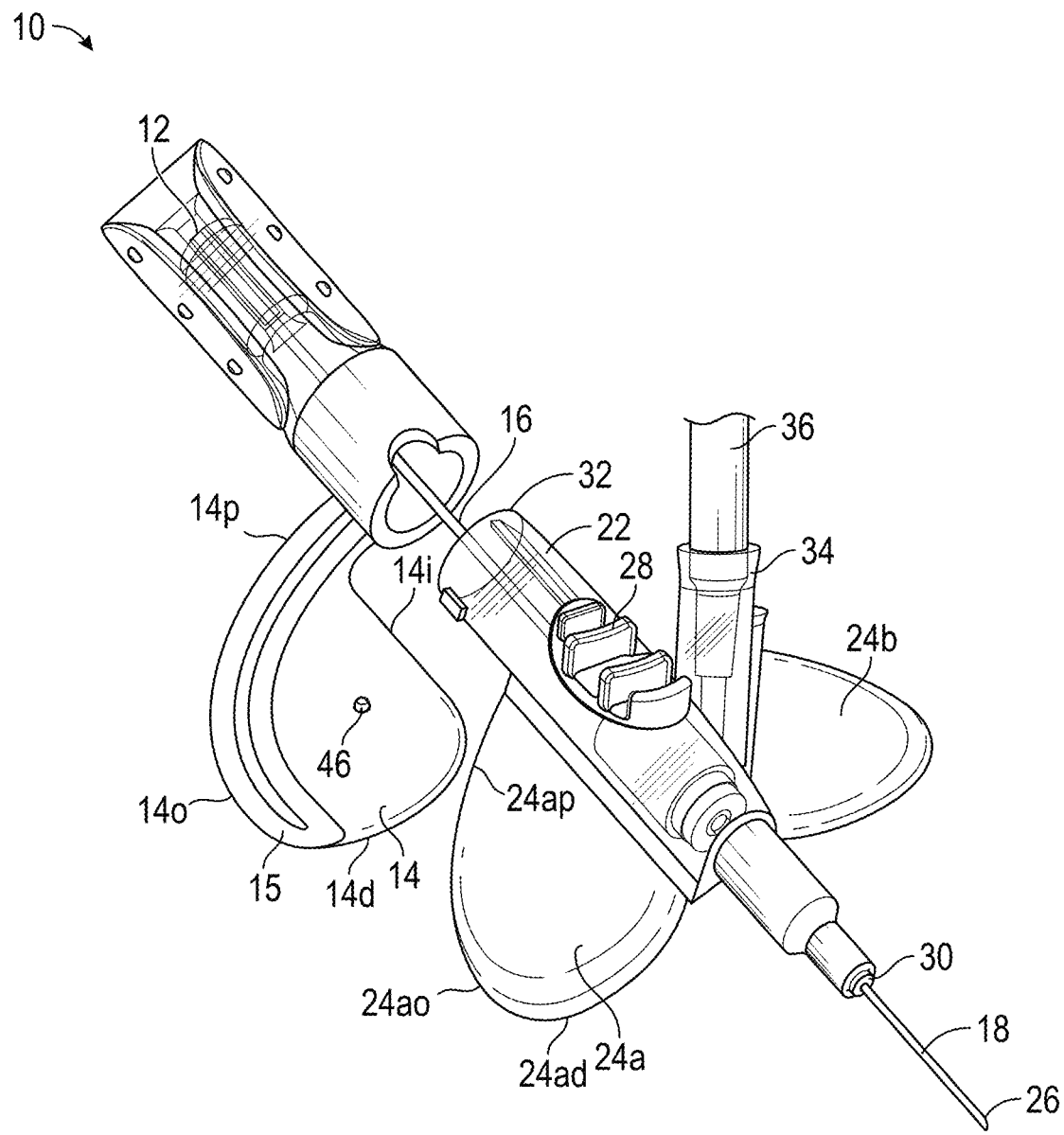
FIG. 3B is an upper perspective view of the catheter system, illustrating the needle hub removed from the catheter adapter, according to some embodiments.
Figure 3C:
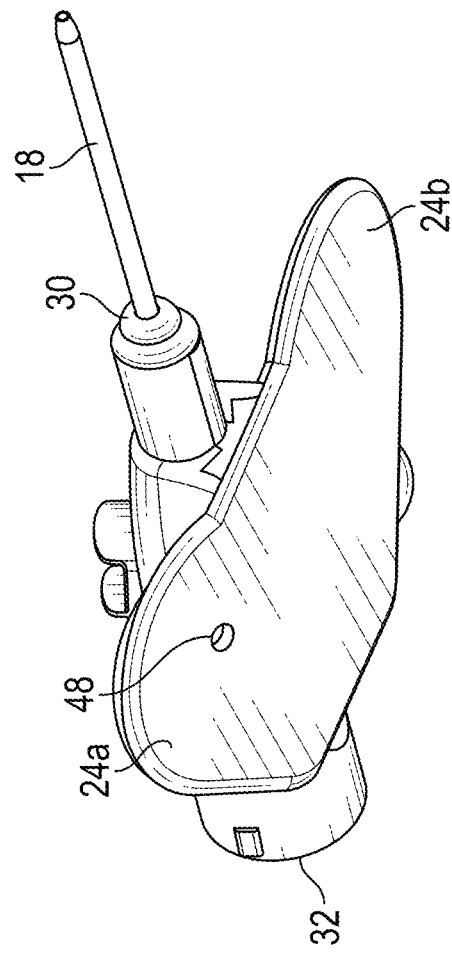
FIG. 3C is a lower perspective view of the catheter system, according to some embodiments.
Figure 3D:
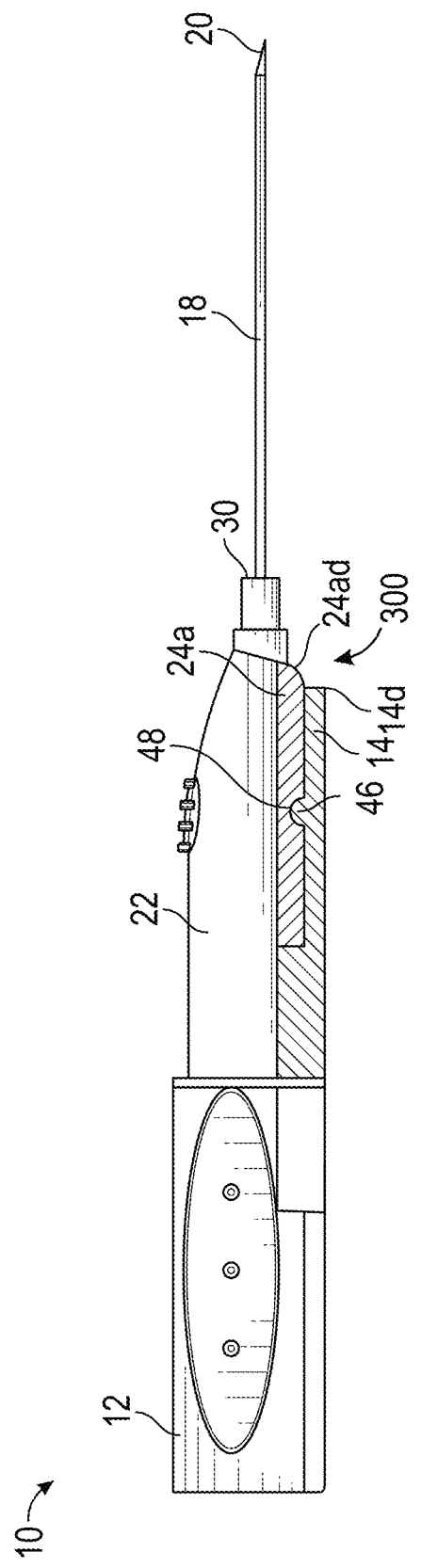
FIG. 3D is a cross-sectional view of the catheter system along line 3D-3D of FIG. 3A, according to some embodiments.
Figure 3E:
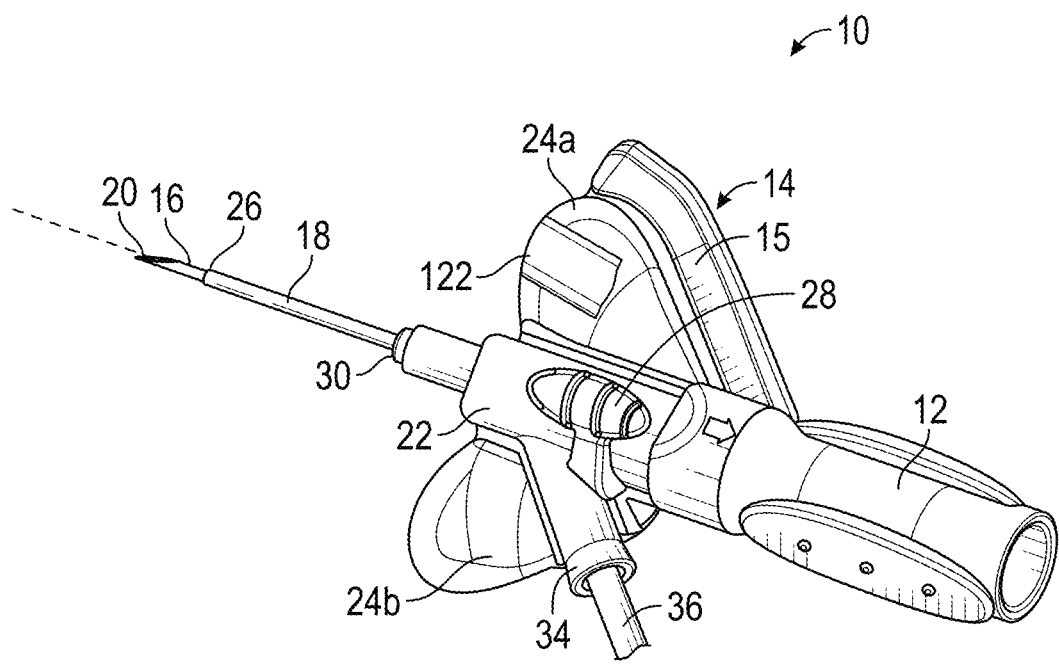

In some embodiments, the slot 40 may include an aperture or hole that may extend through the wing 24a or the paddle 14, as illustrated, for example, in FIGS. 2A-2B. In some embodiments, the slot 40 may include a groove, as illustrated, for example, in FIG. 2E, which may not extend through the wing 24a or the paddle 14.

Referring now to FIGS. 3A-3D, ridge 15 extends upwardly along a proximal edge 14p and an outer edge 140 of paddle 14. An upper surface of paddle 14 includes a flat and smooth paddle portion that extends between ridge 15 and an inner edge 14i and distal edge 14d of paddle 14. Wing24a includes a proximal edge 24ap and an outer edge 24ao that conform to ridge 15 to thereby cause wing 24a to abut ridge 15 when catheter adapter 22 is coupled with needle hub 12. Wing 24a includes a distal edge 24ad positioned beyond distal edge 14d of paddle 14 when proximal edge 24ap and outer edge 24ao of wing 24a abut ridge 15 to thereby form a distal wing portion 300 that is positioned beyond distal edge 14d of paddle 14. A lower surface of wing 24a includes a flat and smooth wing portion that extends between proximal edge 24ap and outer edge 24ao of wing 24a and catheter adapter 22. In in some embodiments, an extension 46 may fit snugly within a groove 48. As an example, the groove 48 may include a socket, and the extension 46 may include a ball shape. In some embodiments, a shape of the groove 48 may correspond to a shape of the extension 46 and/or a diameter of the groove 48 may be approximately equal to a diameter of the extension 46. Thus, in some embodiments, the extension 46 may fit snugly within the groove 48.

In some embodiments, the shape of the groove 48 may prevent the extension 46 from moving axially, particularly when the user pinches the wing 24a and the paddle 14 together. In some embodiments, the groove 48 and the extension 46 may reduce a likelihood of separation of the wing 24a and the paddle 14 during insertion and/or withdrawal of the catheter system 10 with respect to the vasculature. In some embodiments, a force of the thumb of the user in the distal direction may be able to remove the extension 46 from the groove 48 in order to separate the wing 24a and the paddle 14, after the catheter 18 is inserted into the vasculature. In some embodiments, the groove 48 may be replaced with a hole of similar size.

In some embodiments, the extension 46 may extend upwardly from the paddle 14, and the wing 24a may include the groove 48. As stated, in some embodiments, the wing 24a may be constructed of the flexible material such that the wing 24a may be pulled or deflected away from the paddle 14 by the user in order to separate the needle hub 12 from the catheter adapter 22 after insertion of the catheter system 10 within the vasculature is complete. In some embodiments, the extension 46 may extend downwardly from the wing 24a, and the paddle 14 may include the groove 48.

Referring now to FIGS. 4A-4D, in some embodiments, the catheter system 10 may include one or more grooves 50 and/or one or more ribs 52. In some embodiments, the ribs 52 may be disposed within the grooves 50. In some embodiments, the grooves 50 and/or the ribs 52 may extend generally perpendicular to a longitudinal axis 44 of the catheter system 10. In some embodiments, the ribs 52 and/or the grooves 50 may reduce a likelihood of separation of the wing 24a and the paddle 14 during insertion and/or withdrawal of the catheter system 10 with respect to the vasculature, particularly when the user pinches the wing 24a and the paddle 14 together. In some embodiments, the ribs 52 and/or the grooves 50 may provide resistance to the wing 24a moving in the proximal direction and the distal direction with respect to the paddle 14. In some embodiments, a force of the thumb of the user in the distal direction may be able to remove the ribs 52 from the grooves 50 in order to separate the wing 24a and the paddle 14, after the catheter 18 is inserted into the vasculature.

Figure 4A:
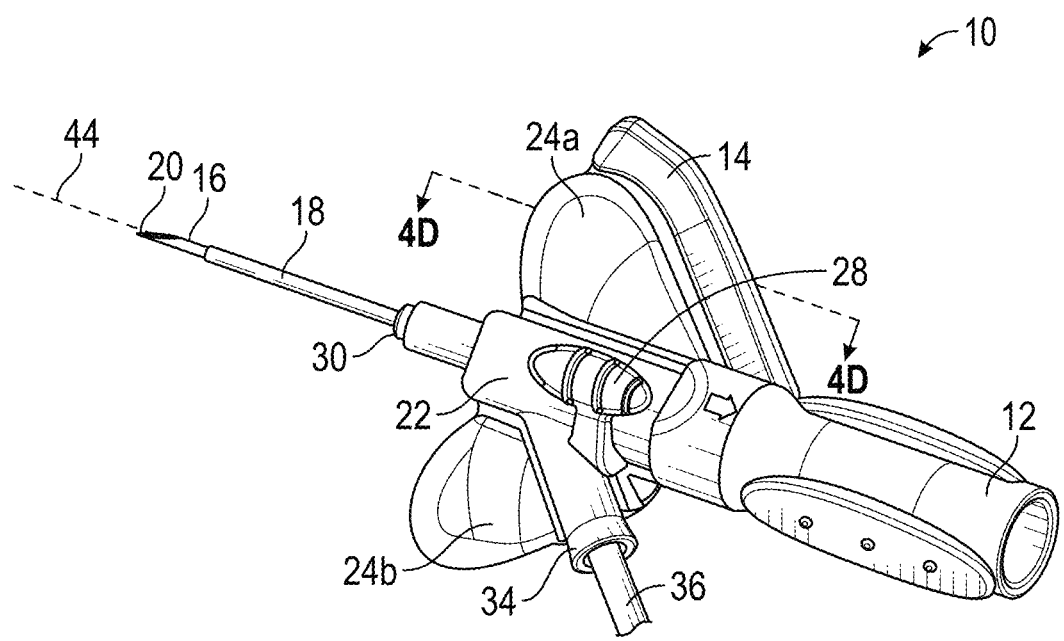
FIG. 4A is an upper perspective view of the catheter system, according to some embodiments.
Figure 4B:
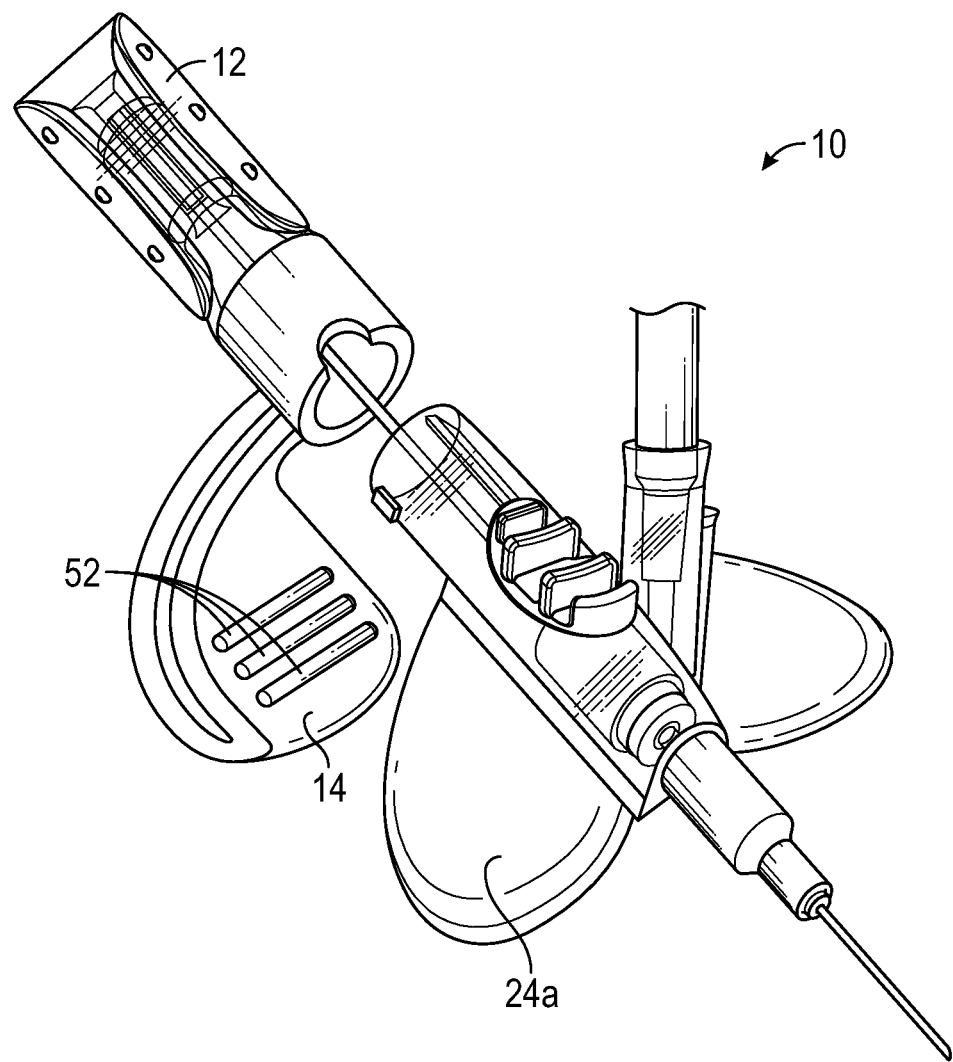
FIG. 4B is an upper perspective view of the catheter system, illustrating the needle hub removed from the catheter adapter and example ribs, according to some embodiments.

In some embodiments, the ribs 52 may extend outwardly from a top of the paddle 14, and the bottom 38a of the wing 24a may include the grooves 50, as illustrated, for example, in FIGS. 4B-4D. In some embodiments, the ribs 52 may extend outwardly from the bottom 38a of the wing 24a, and the top of the paddle 14 may include the grooves 50. In some embodiments, the catheter system 10 may include the ribs 52 but not the grooves 50. In some embodiments, the ribs 52 may increase friction and decrease movement between the wing 24a and the paddle 14. In some embodiments, the wing 24a may be constructed of the flexible material such that the wing 24a may be pulled or deflected away from the paddle 14 by the user in order to separate the needle hub 12 from the catheter adapter 22 after insertion of the catheter system 10 within the vasculature is complete.

Referring now to FIGS. 5A-5E, in some embodiments, the catheter system 10 may include a chevron pattern surface 54 and a corresponding chevron pattern surface 56. In some embodiments, the chevron pattern surface 54 may be substantially identical to the corresponding chevron pattern surface 56. In some embodiments, the chevron pattern surface 54 may be offset from the corresponding chevron pattern surface 56 such that the chevron pattern surface 54 fits within the corresponding chevron pattern surface 56. In some embodiments, the bottom 38a of the wing 24a may include the chevron pattern surface 54 or the corresponding chevron pattern surface 56. In some embodiments, the top of the paddle 14 may include the chevron pattern surface 54 or the corresponding chevron pattern surface 56. In some embodiments, the chevron pattern surface 54 and/or the corresponding chevron pattern surface 56 may be formed of extensions with grooves disposed in between the extensions.

In some embodiments, the chevron pattern surface 54 and the corresponding chevron pattern surface 56 may extend generally perpendicular to the longitudinal axis 44 of the catheter system 10. In some embodiments, the chevron pattern surface 54 and the corresponding chevron pattern surface 56 may reduce a likelihood of separation of the wing 24a and the paddle 14 during insertion and/or withdrawal of the catheter system 10 with respect to the vasculature. In some embodiments, the chevron pattern surface 54 and the corresponding chevron pattern surface 56 may prevent the wing 24a from moving in the proximal direction and the distal direction with respect to the paddle 14 when the user pinches the wing 24a and the paddle 14 together during insertion and/or withdrawal.

In some embodiments, after the catheter 18 is inserted into the vasculature a force of the thumb of the user in the distal direction may move the chevron pattern surface 54 with respect to the corresponding chevron pattern surface 56 in order to separate the wing 24a and the paddle 14. In some embodiments, the wing 24a may be constructed of the flexible material such that the wing 24a may be pulled or deflected away from the paddle 14 by the user in order to separate the needle hub 12 from the catheter adapter 22 after insertion of the catheter system 10 within the vasculature is complete.

Figure 5A:
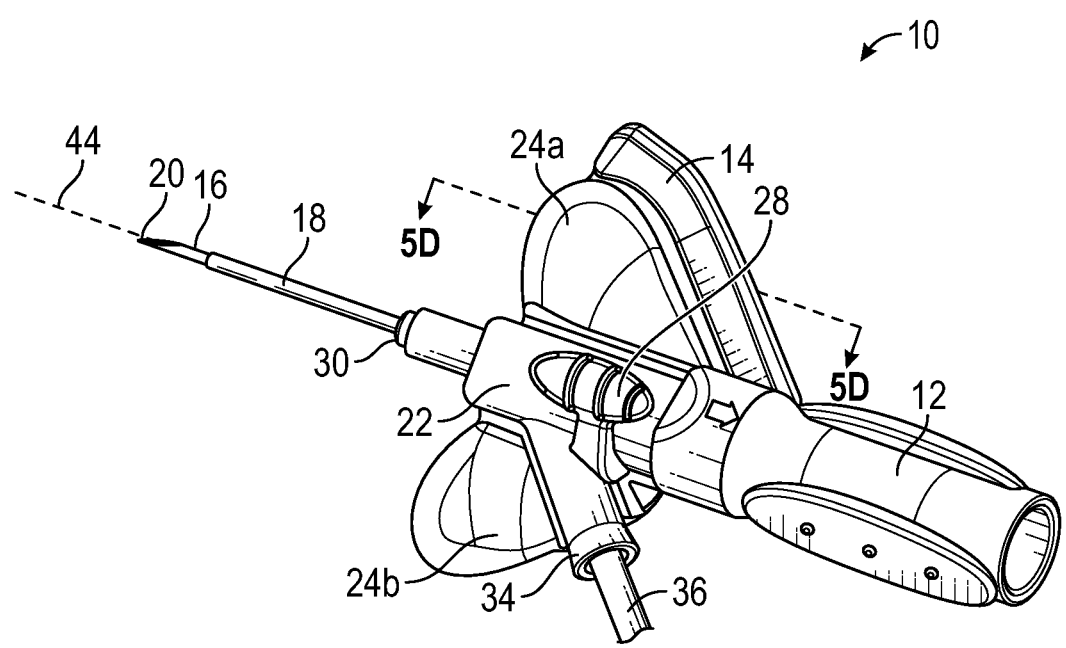
FIG. 5A is an upper perspective view of the catheter system, according to some embodiments.
Figure 5B:
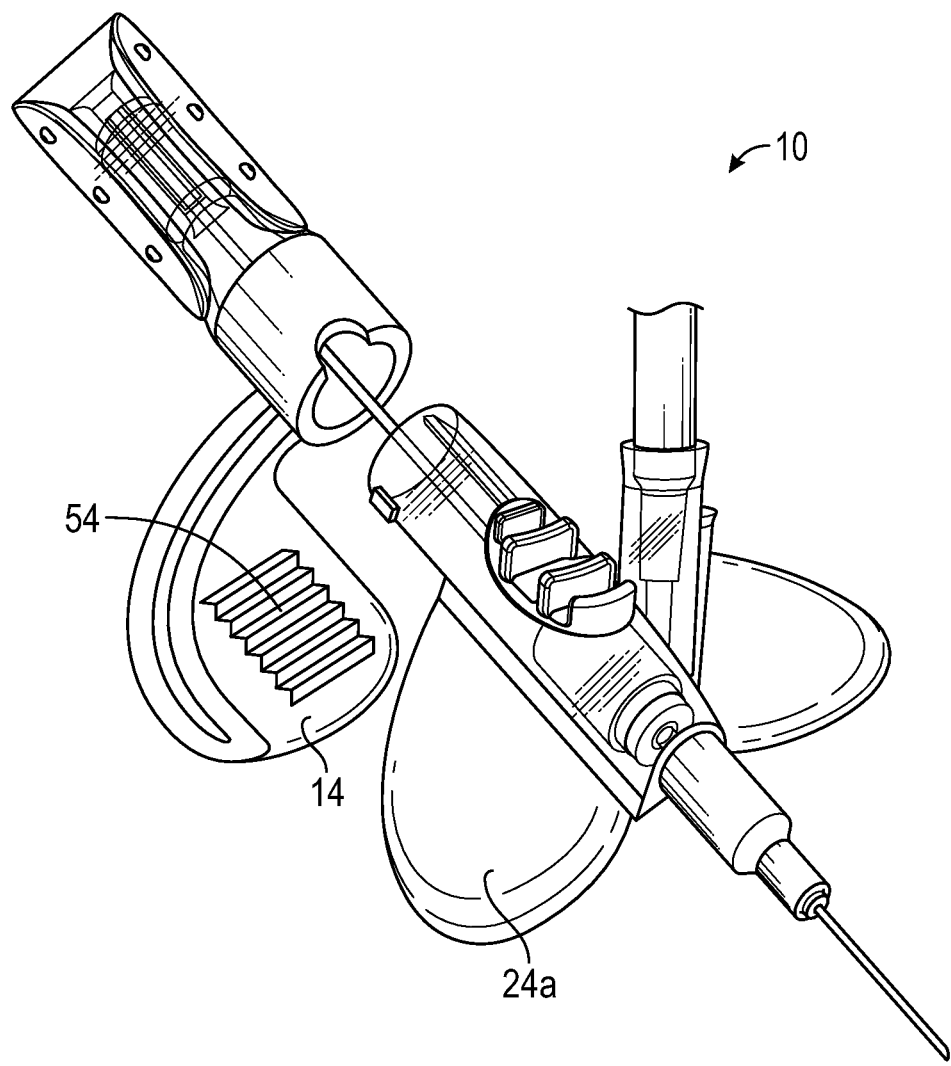
FIG. 5B is an upper perspective view of the catheter system, illustrating the needle hub removed from the catheter adapter and an example chevron pattern surface, according to some embodiments.
Figure 5C:
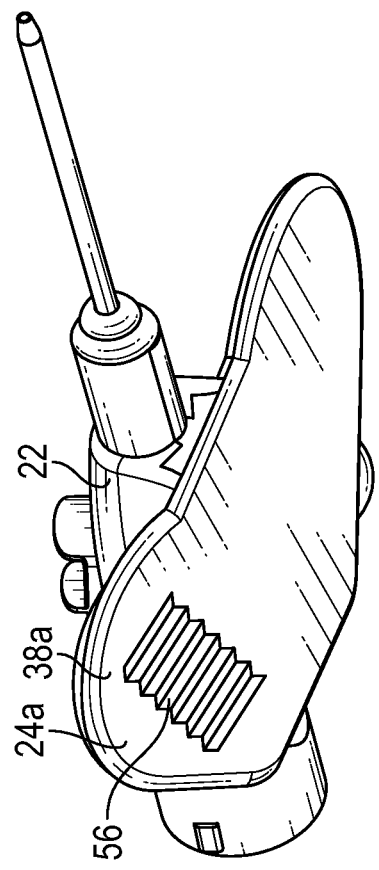
FIG. 5C is a lower perspective view of the catheter system, according to some embodiments.
Figure 5D:
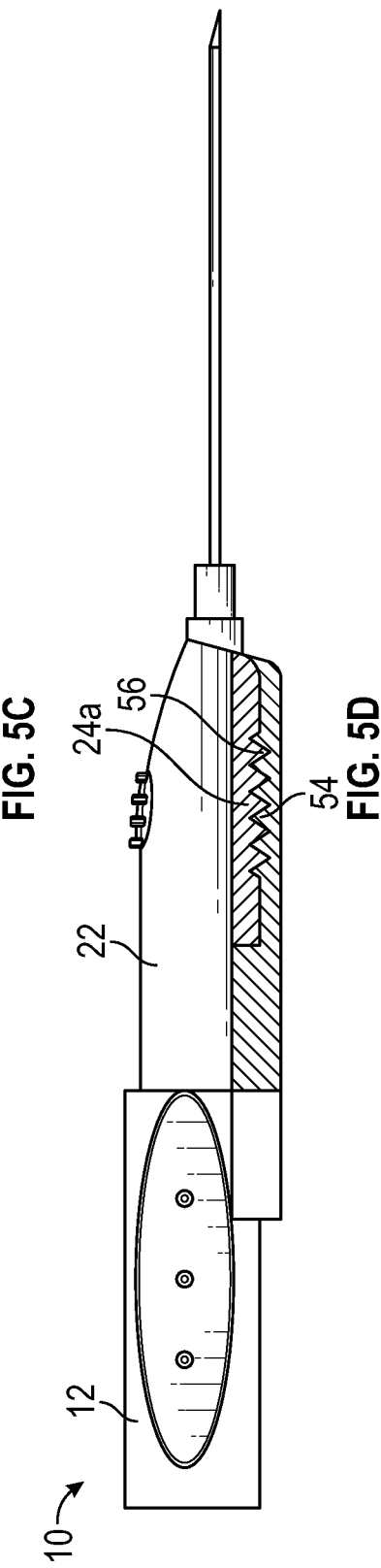
FIG. 5D is a cross-sectional view of the catheter system along line 5D-5D of FIG. 5A, according to some embodiments.
Figure 5E:
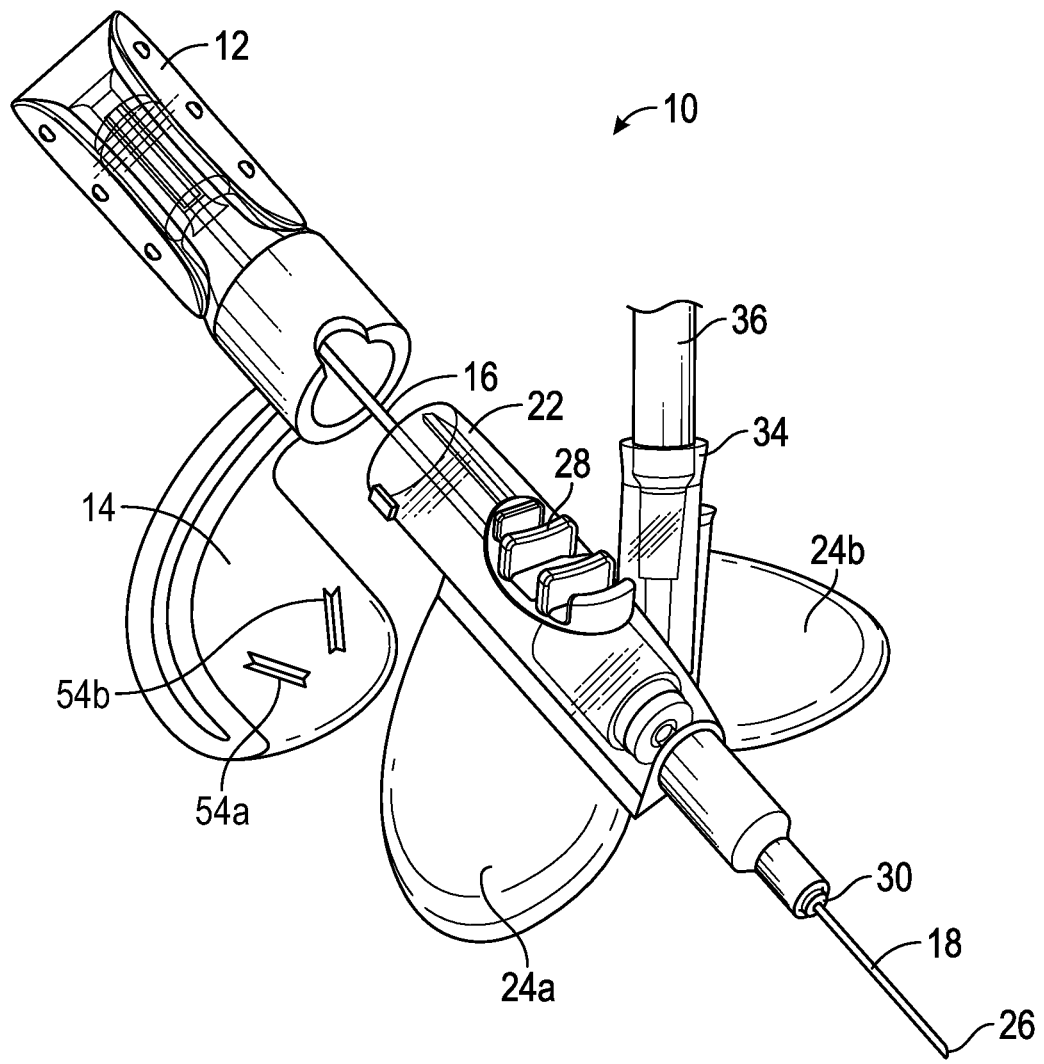
FIG. 5E is an upper perspective view of the catheter system, illustrating the needle hub removed from the catheter adapter and another example chevron pattern surface, according to some embodiments.

As illustrated in FIG. 5E, in some embodiments, the chevron pattern surface 54 may be generally V-shaped, and the corresponding chevron pattern surface 54 may also be V-shaped. In further detail, in some embodiments, the chevron pattern surface 54 may include one or more first grooves and/or one or more first extensions 54a oriented in a first direction. Additionally, in some embodiments, the chevron pattern surface 54 may include one or more second grooves and/or one or more second extensions 54b oriented in a second direction to form a general V-shape. In some embodiments, the general V-shape of the chevron pattern surface 54 may facilitate an initial interlock between the chevron pattern surface 54 and the corresponding chevron pattern surface 54, during insertion of the catheter system 10, for example, but in response to the chevron pattern surface 54 being released from the corresponding chevron pattern surface 54 there may be reduced catching and increased free gliding between the chevron pattern surface 54 and the corresponding chevron pattern surface 54.

Referring now to FIG. 6, in some embodiments, the bottom 38a of the wing 24a and the top of the paddle 14 may be ramped. In some embodiments, a thickness of a ramped surface 58 of the paddle 14 may be greater at a distal end of the ramped surface 58 than at a proximal end of the ramped surface 58 such that the wing 24a resists movement in the distal direction. In some embodiments, a ramped surface 60 of the wing 24a may contact the ramped surface 58 along all or a portion of a length of the ramped surface 58. In some embodiments, a thickness of a ramped surface 60 of the wing 24a may be greater at a proximal end of the ramped surface 60 than at a distal end of the ramped surface 60.

In some embodiments, the ramped surface 58 and the ramped surface 60 may reduce a likelihood of separation of the wing 24a and the paddle 14 during insertion and/or withdrawal of the catheter system 10 with respect to the vasculature, particularly when the user pinches the wing 24a and the paddle 14 together. In some embodiments, a force of the thumb of the user in the distal direction may be able to overcome the ramped surface 58 in order to separate the wing 24a and the paddle 14, after the catheter 18 is inserted into the vasculature.

Figure 7:
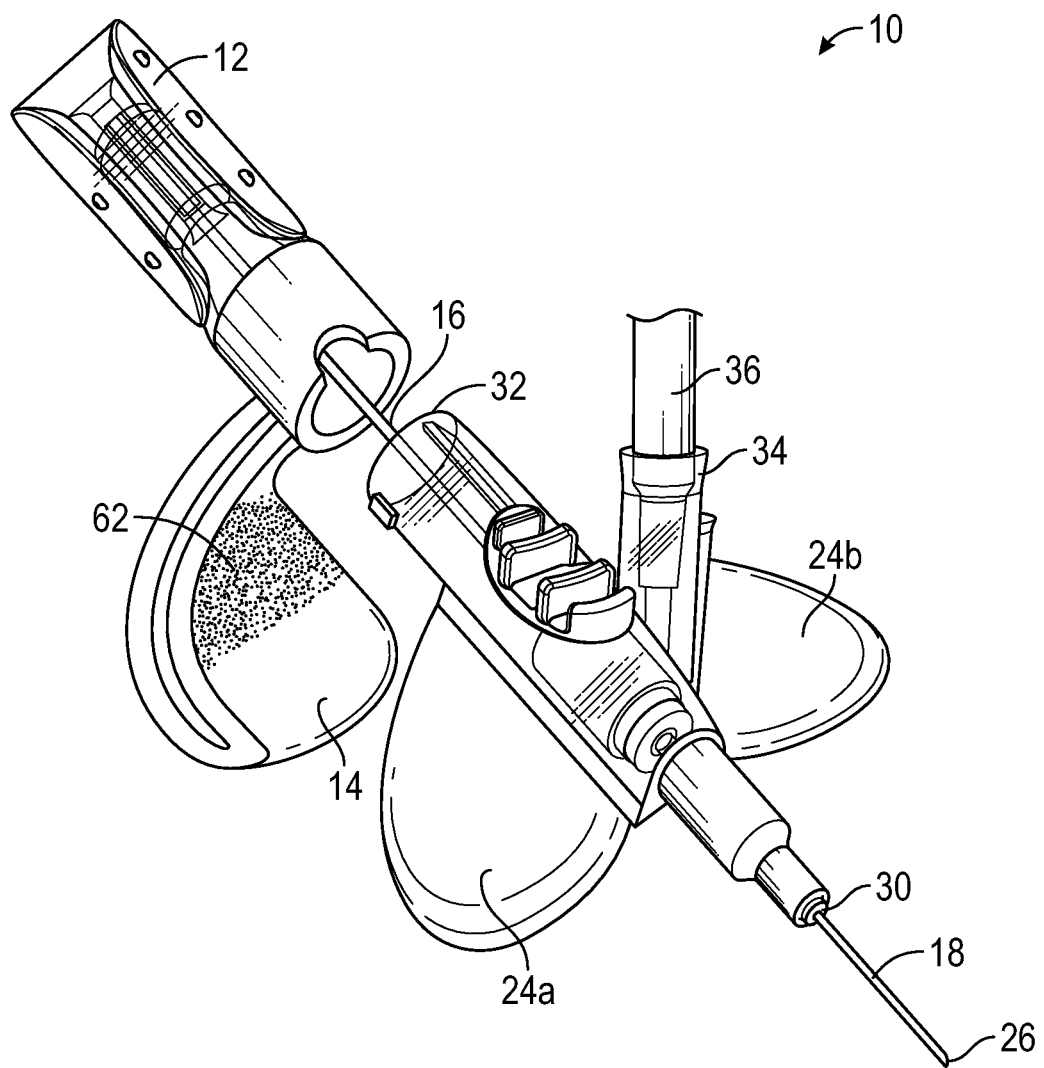
FIG. 7 is an upper perspective view of the catheter system, illustrating the needle hub removed from the catheter adapter and an example rough texture, according to some embodiments.

Referring now to FIG. 7, in some embodiments, the top of the paddle 14 and/or the bottom 38a of the wing 24a may include a rough texture 62, which may provide resistance to the wing 24a moving in the proximal direction and/or the distal direction with respect to the paddle 14, particularly when the user pinches the wing 24a and the paddle 14 together during insertion of the catheter 18 into the vasculature.

In some embodiments, the rough texture 62 may be disposed on a proximal portion of side of the paddle 14 and/or the wing 24a. In some embodiments, a distal portion or side of the paddle 14 and/or the wing 24a may be smooth. In some embodiments, the rough texture 62 may be disposed on the top of the paddle 14 and may be tall enough to embed in the flexible material of the wing 24a. In some embodiments, the rough texture 62 may be rigid.

Figure 8A:
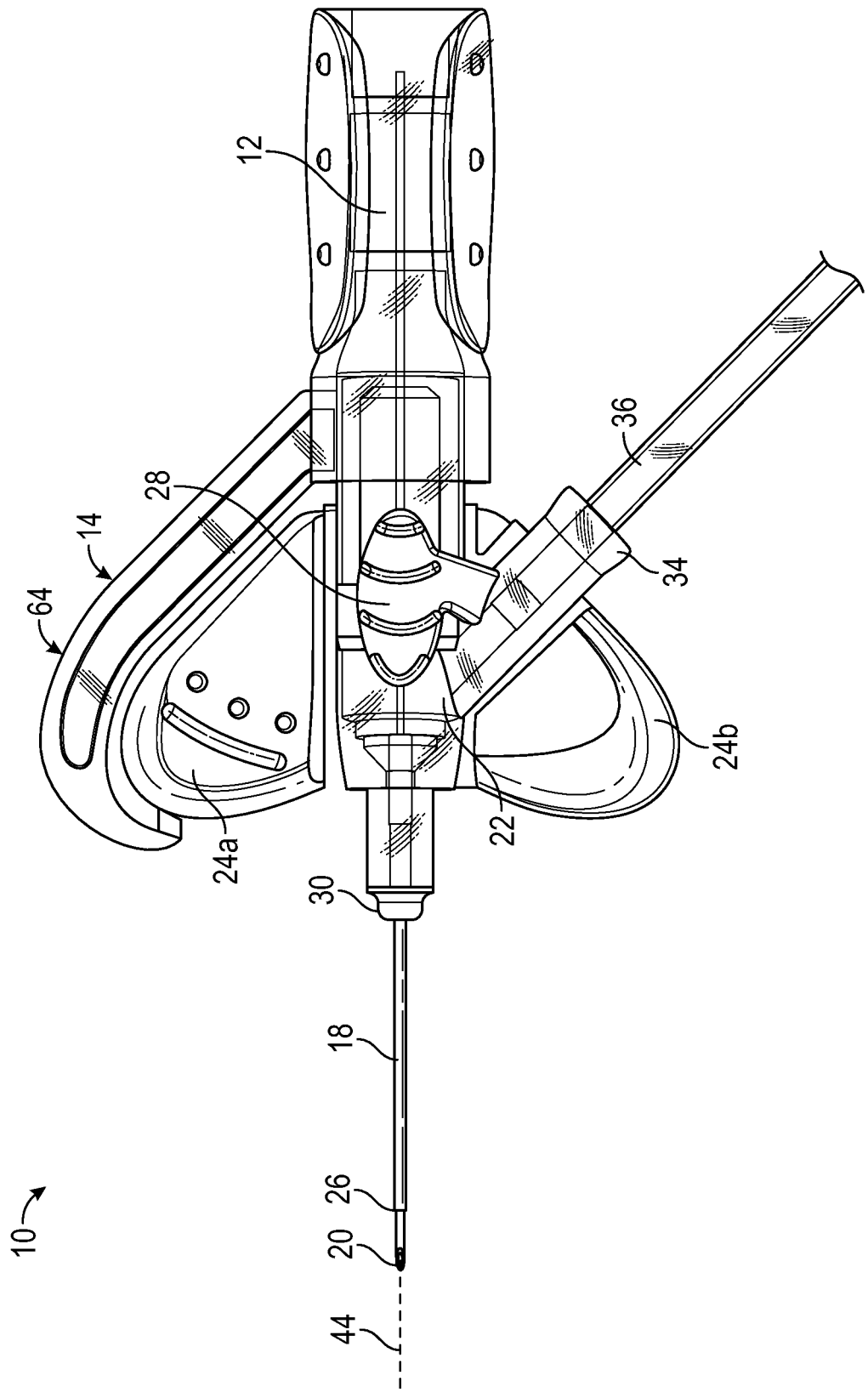
FIG. 8A is a top view of the catheter system, illustrating an example arm, according to some embodiments.
Figure 8B:
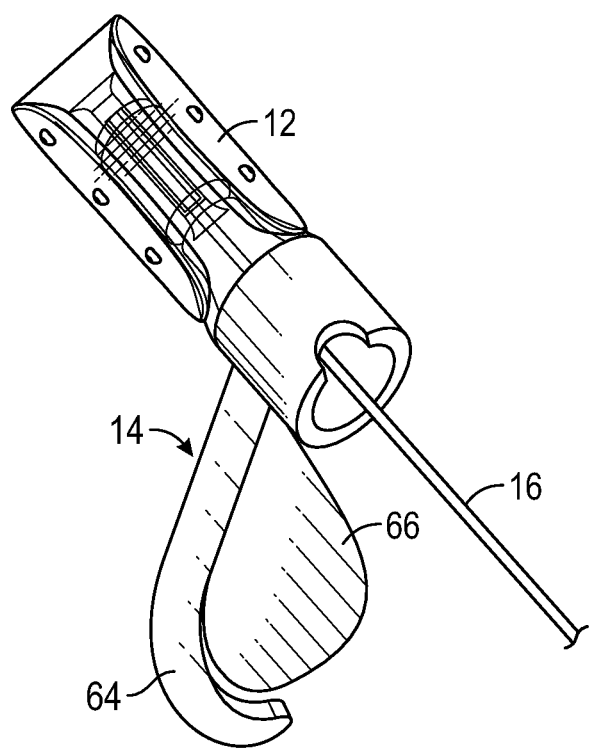
FIG. 8B is an upper perspective view of an example needle hub, illustrating the arm, according to some embodiments.

Referring now to FIGS. 8A-8B, in some embodiments, the paddle 14 may include an arm 64, which may be separated from a portion 66 of the paddle 14 that sits underneath the wing 24a such that the arm 64 may move independently of the portion of the paddle 14 that sits underneath the wing 24a. In some embodiments, the arm 64 may be movable between a first position, in which distal movement of the wing 24a and the catheter adapter 22 is prevented, and a second position, in which distal movement of the wing 24a and the catheter adapter 22 is allowed. In some embodiments, when the arm 64 is in the first position, a distal end of the wing 24a may contact the arm 64. In some embodiments, when the arm 64 is in the second position, the arm 64 may be disposed below the wing 24a, such that the wing 24a may move distally. In some embodiments, a curvature of the arm 64 may generally mirror a curvature of an outer edge of the wing 24a.

Figure 9A:
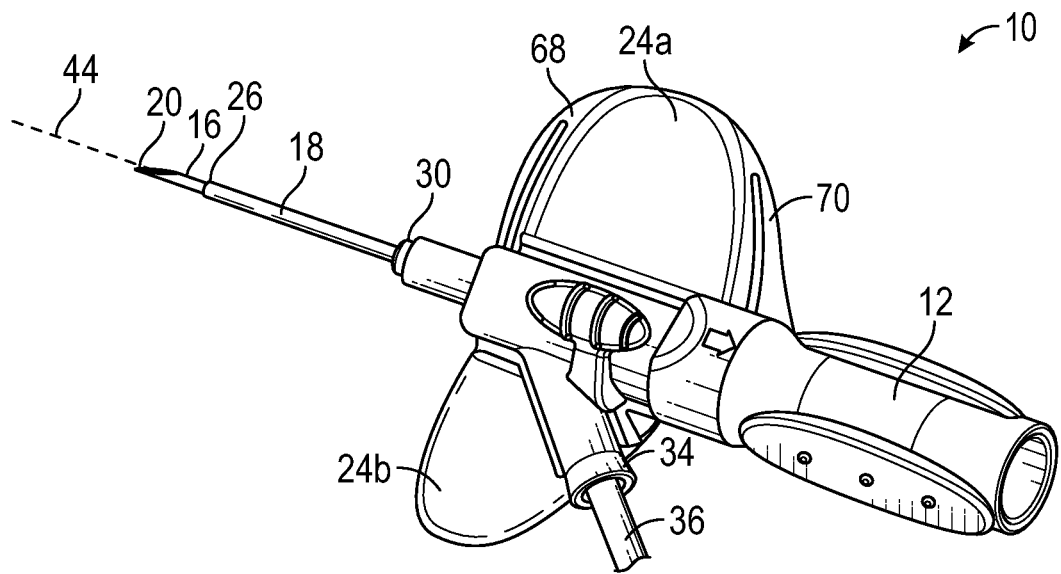
FIG. 9A is an upper perspective view of the catheter system, illustrating an example raised distal edge and an example raised proximal edge, according to some embodiments.
Figure 9B:
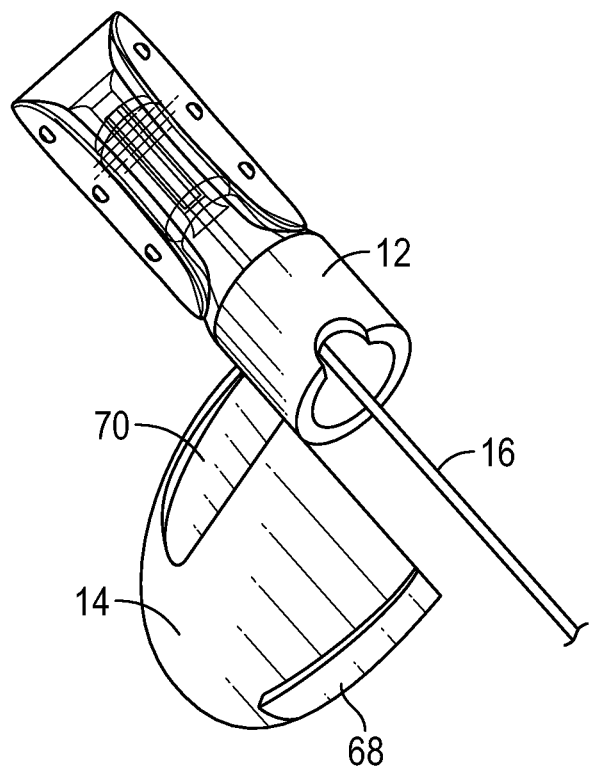
FIG. 9B is an upper perspective view of the needle hub, illustrating the example raised distal edge and the example raised proximal edge, according to some embodiments.

Referring now to FIGS. 9A-9B, in some embodiments, the wing 24a may be disposed between a raised distal edge 68 of the paddle 14 and/or a raised proximal edge 70 of the paddle 14. In some embodiments, the raised distal edge 68 and/or the raised proximal edge 70 may reduce a likelihood of separation of the wing 24a and the paddle 14 during insertion and/or withdrawal of the catheter system 10 with respect to the vasculature of the patient.

In some embodiments, to advance the catheter 18 distally after insertion of the catheter 18 into the vasculature and/or to remove the needle hub 12 from the catheter adapter 22, the user may lift and slightly rotate the wing 24a to overcome the raised distal edge 68. In some embodiments, the raised distal edge 68 may be tapered such that an outer portion of the raised proximal edge 70 is thicker than an inner portion of the raised proximal edge 70. In some embodiments, the raised proximal edge 70 may be tapered such that an outer portion of the raised proximal edge 70 is thicker than an inner portion of the raised proximal edge 70. In some embodiments, the raised distal edge 68 may be connected to the raised proximal edge 70 by a raised intermediate edge, such that the raised distal edge 68, the raised intermediate edge, and the raised proximal edge 70 form a U-shape around the wing 24a (not illustrated).

Figure 10A:
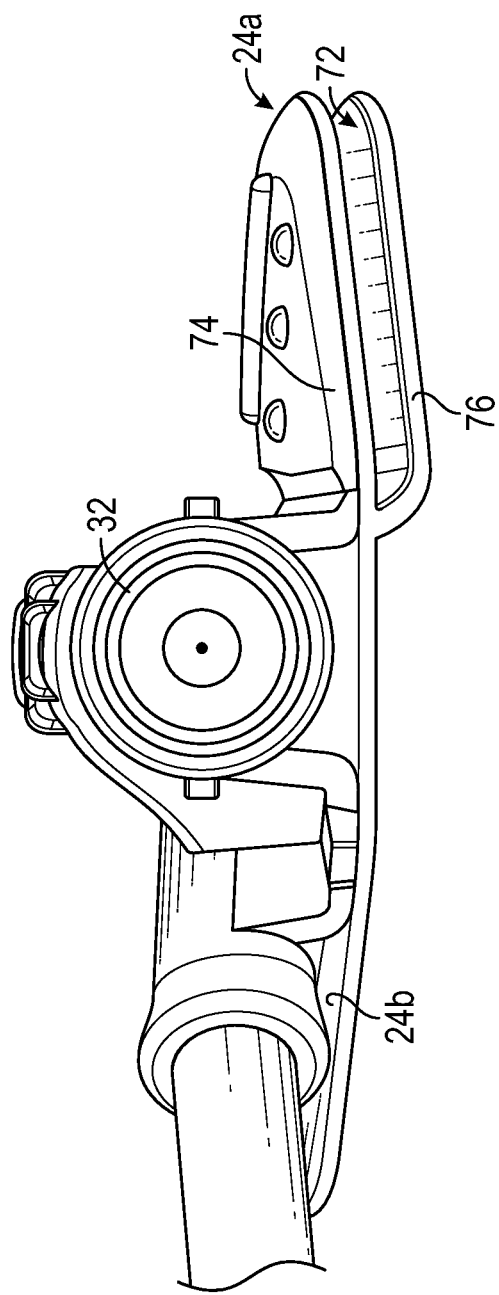
FIG. 10A is a proximal end view of the catheter system, illustrating the wing having an example upper portion and an example lower portion, an according to some embodiments.
Figure 10B:
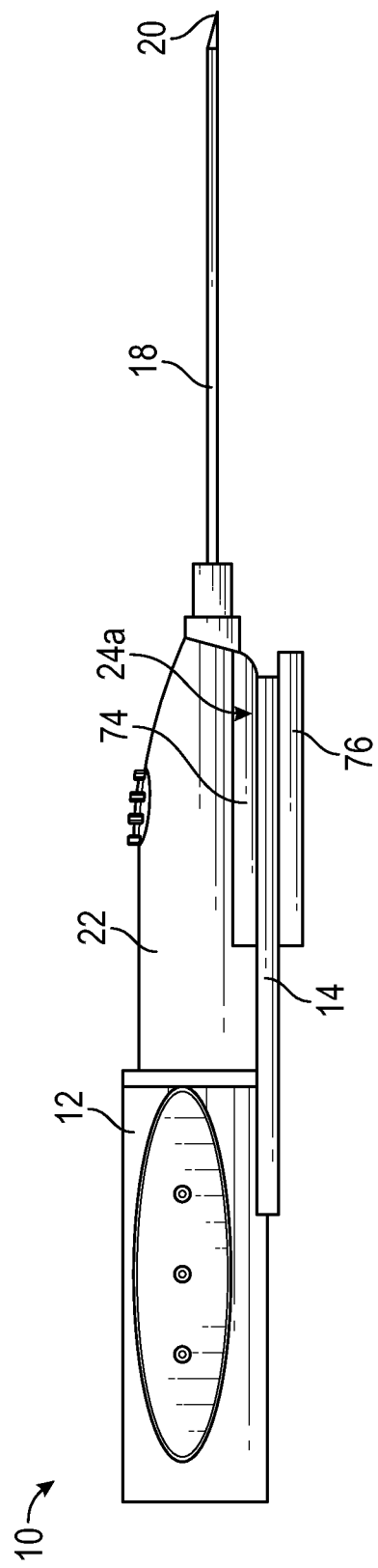
FIG. 10B is a side view of the catheter system, according to some embodiments.

Referring now to FIGS. 10A-10B, in some embodiments, the wing 24a may include a slot 72 disposed between an upper portion 74 and a lower portion 76 of the wing 24a. In some embodiments, the paddle 14 may be disposed in the slot 72. In some embodiments, the wing 24a may be disposed above and below the paddle 14. In some embodiments, the user may pinch an upper portion 74 and a lower portion 76 of the wing 24a together to prevent movement of the paddle 14 with respect to the wing 24a during insertion and/or withdrawal of the catheter system 10 with respect to the vasculature.

Figure 11A:
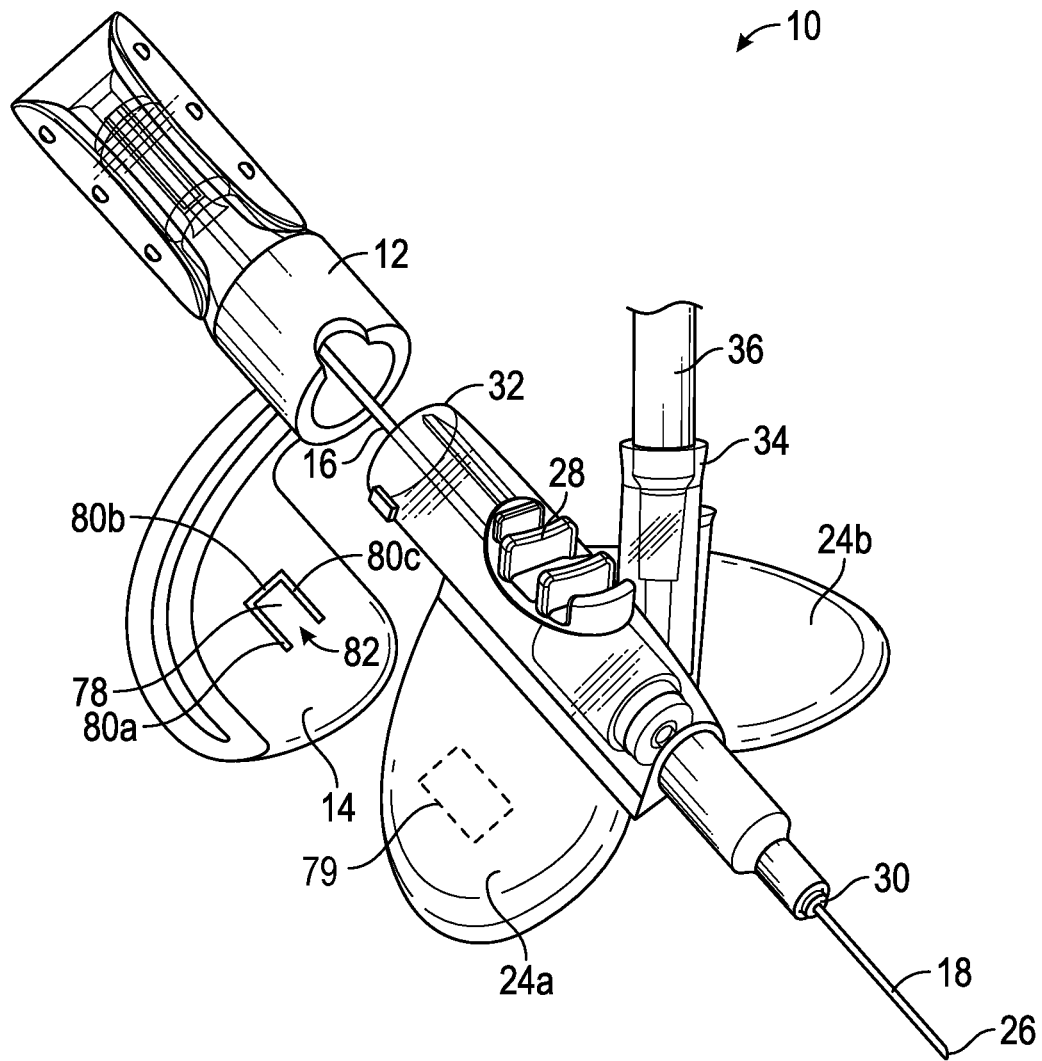
FIG. 11A is an upper perspective view of the catheter system, illustrating the needle hub removed from the catheter adapter and an example cantilever element, according to some embodiments.
Figure 11B:
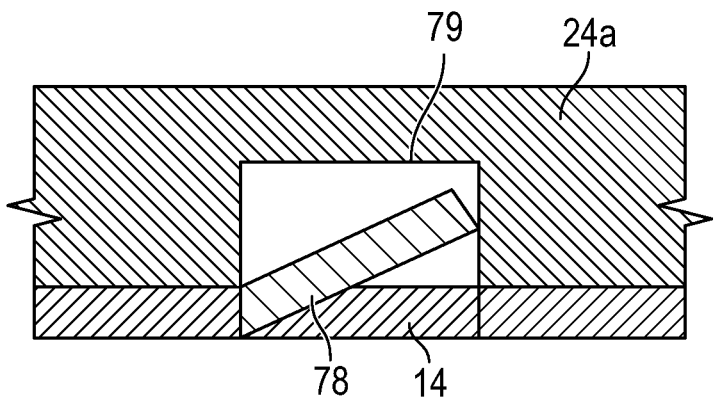
FIG. 11B is an enlarged cross-sectional view of the cantilever element disposed within an example recess, according to some embodiments.

Referring now to FIGS. 11A-11B, in some embodiments, the catheter system 10 may include a cantilever element 78 and a groove or recess 79 configured to receive the cantilever element 78. In some embodiments, the paddle 14 may include the cantilever element 78 and the bottom 38a of the wing 24a may include the recess 79. In some embodiments, the cantilever element 78 may not be disposed within the recess 79. In these embodiments, the cantilever element 78 may be inserted into the recess 79 in response to the user pinching the wing 24a and the paddle 14 together and pressing upwardly on the cantilever element 78 during insertion of the catheter 18 into the vasculature.

In some embodiments, one or more sides 80a, 80b, 80c of the cantilever element 78 may be cut out from the paddle 14 to allow movement of the cantilever element 78. In some embodiments, the cantilever element 78 may be configured to bend at a base 82 of the cantilever element 78 proximate the sides of the cantilever element 78. In some embodiments, the cantilever element 78 may be elongated, as illustrated in FIG. 11, for example, which may facilitate securement of the cantilever element 78 within the recess 79 in response to movement by the user. In some embodiments, the cantilever element 78 may include any suitable shape. In some embodiments, the cantilever element 78 may be generally level with a portion of the wing 34a surrounding the cantilever element 78 when the user is not biasing the cantilever element 78 upward into the recess 79.

Figure 12A:
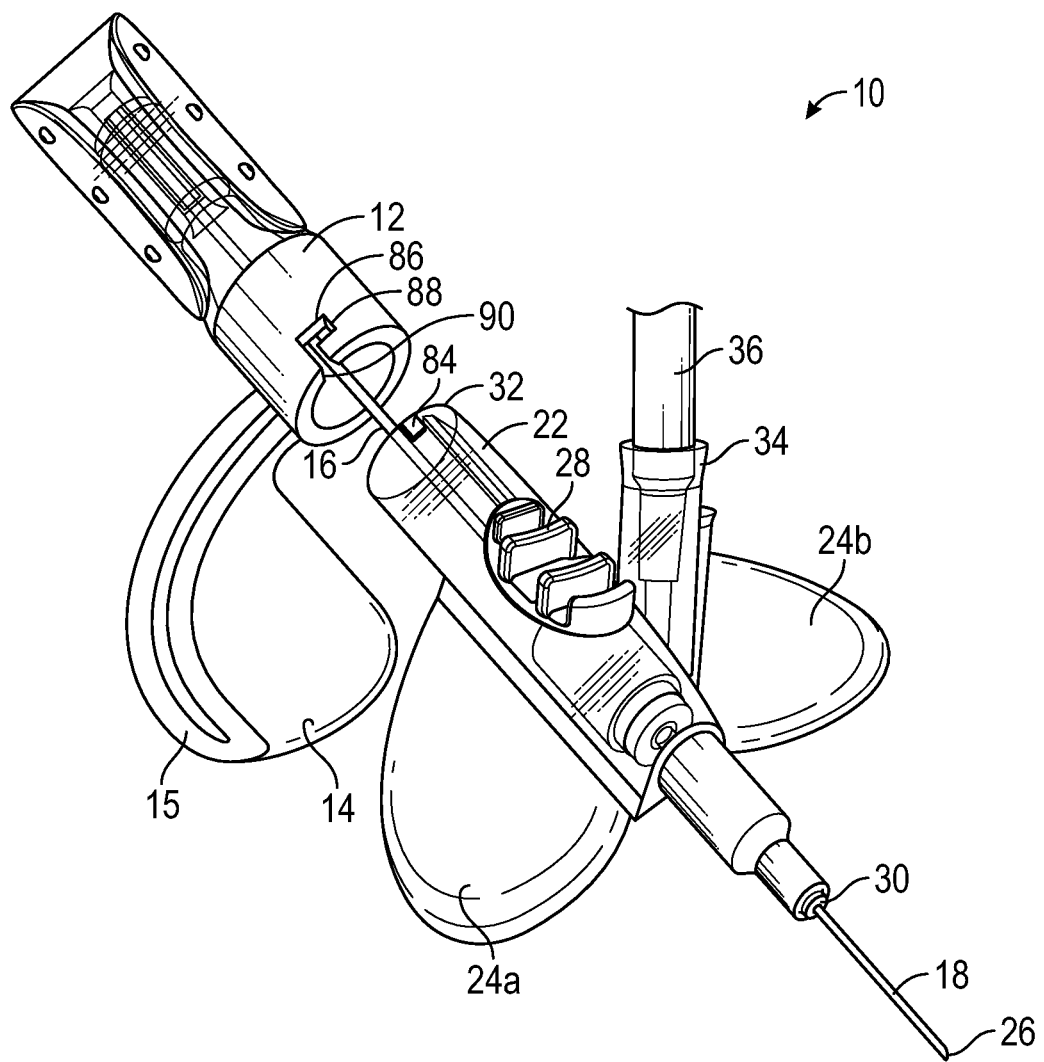
FIG. 12A is an upper perspective view of the catheter system, illustrating the needle hub removed from the catheter adapter and an example slot, according to some embodiments.
Figure 12B:
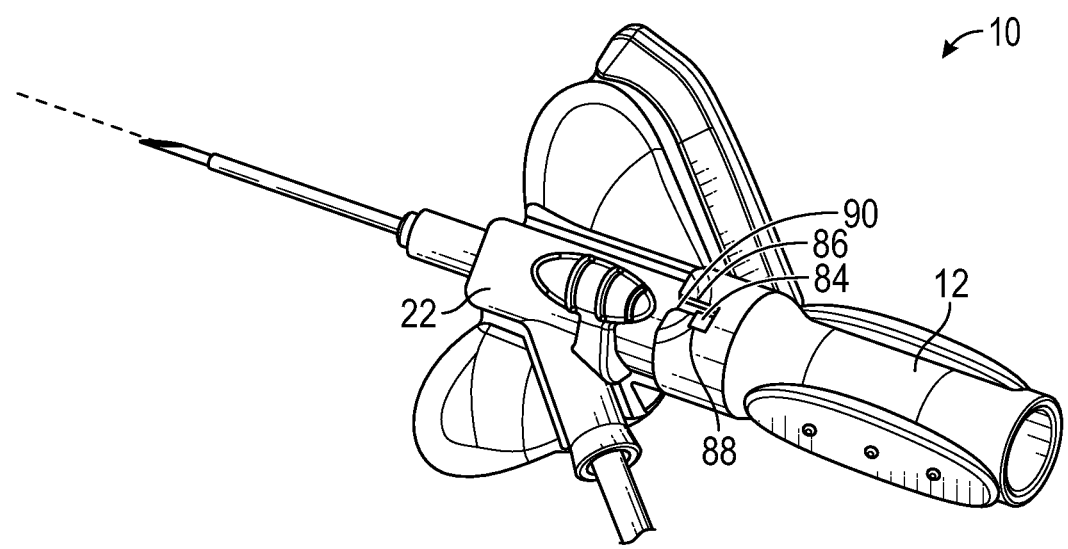
FIG. 12B is an upper perspective view of the catheter system, illustrating an example protrusion disposed at an end of the slot, according to some embodiments.

Referring now to FIGS. 12A-12B, in some embodiments, an outer surface of the catheter adapter 22 may include a protrusion 84, and the needle hub 12 may include a slot 86 configured to receive the protrusion 84. In some embodiments, the slot 86 may include an L-shape. In some embodiments, the protrusion 84 may be disposed at an end 88 of the L-shape. In some embodiments, in response to the protrusion 84 being disposed at the end 88 of the L-shape, the needle hub 12 and the catheter adapter 22 may be prevented from separating and moving axially with respect to each other. In some embodiments, in order to remove the protrusion 84 from the L-shape and separate the catheter adapter 22 from the needle hub 12, the user may rotate the catheter adapter 22 to remove the protrusion from the end 88 of the L-shape and align the protrusion with an opening 90 of the L-shape opposite the end 88 of the L-shape.

Figure 13:
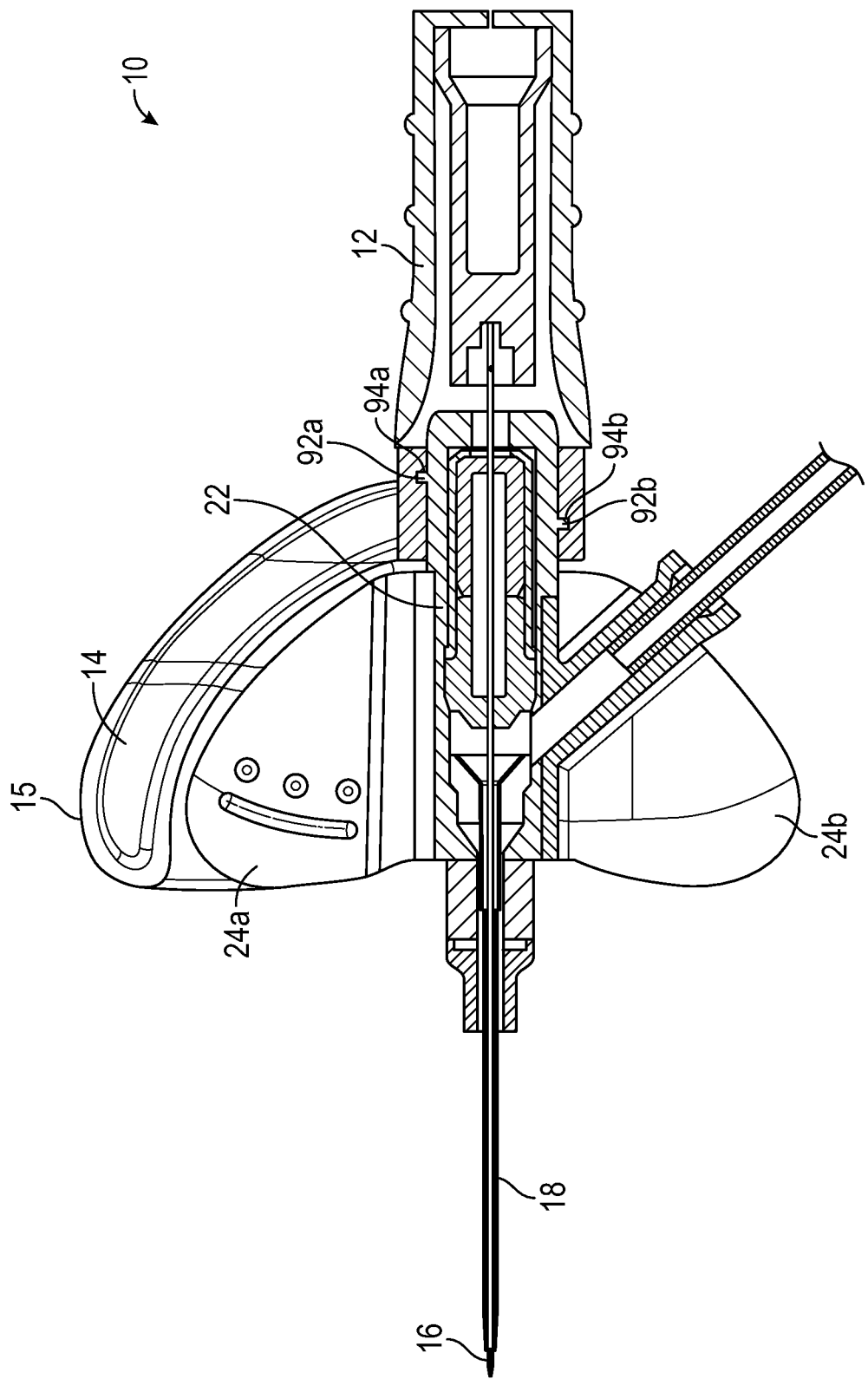
FIG. 13 is a cross-sectional view of the catheter system, illustrating example protrusions, according to some embodiments.

Referring now to FIG. 13, in some embodiments, an outer surface of the catheter adapter 22 may include one or more protrusions 92a, 92b, which may extend radially outward from the outer surface of the catheter adapter 22. In some embodiments, one of the protrusions 92a may be offset from another of the protrusions 92b such that the protrusion 92a is proximal to the protrusion 92b. In some embodiments, the protrusions 92a, 92b may be secured in one or more grooves 94a, 94b of the needle hub 12. In some embodiments, because the protrusions 92a, 92b are offset, if there is slight rotation of the catheter adapter 22 and the needle hub 12 with respect to each other during insertion and/or withdrawal of the catheter system 10 with respect to the vasculature, the needle hub 12 and the catheter adapter 22 may not separate. In some embodiments, in order to separate the catheter adapter 22 and the needle hub 12, the user may rotate the needle hub 12 such that the protrusions 92a, 92b are removed from the grooves 94a, 94b.

Figure 14A:
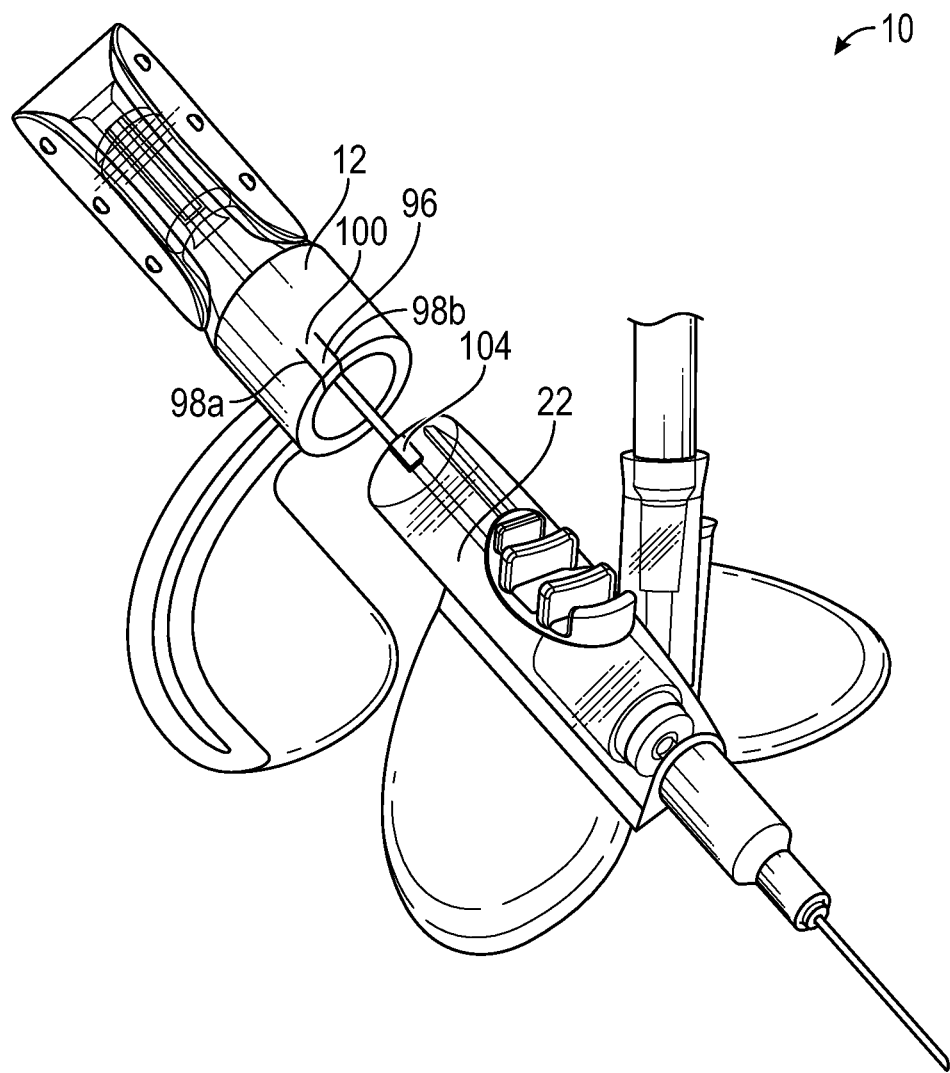
FIG. 14A is an upper perspective view of the catheter system, illustrating the needle hub removed from the catheter adapter and an example arm, according to some embodiments.
Figure 14B:
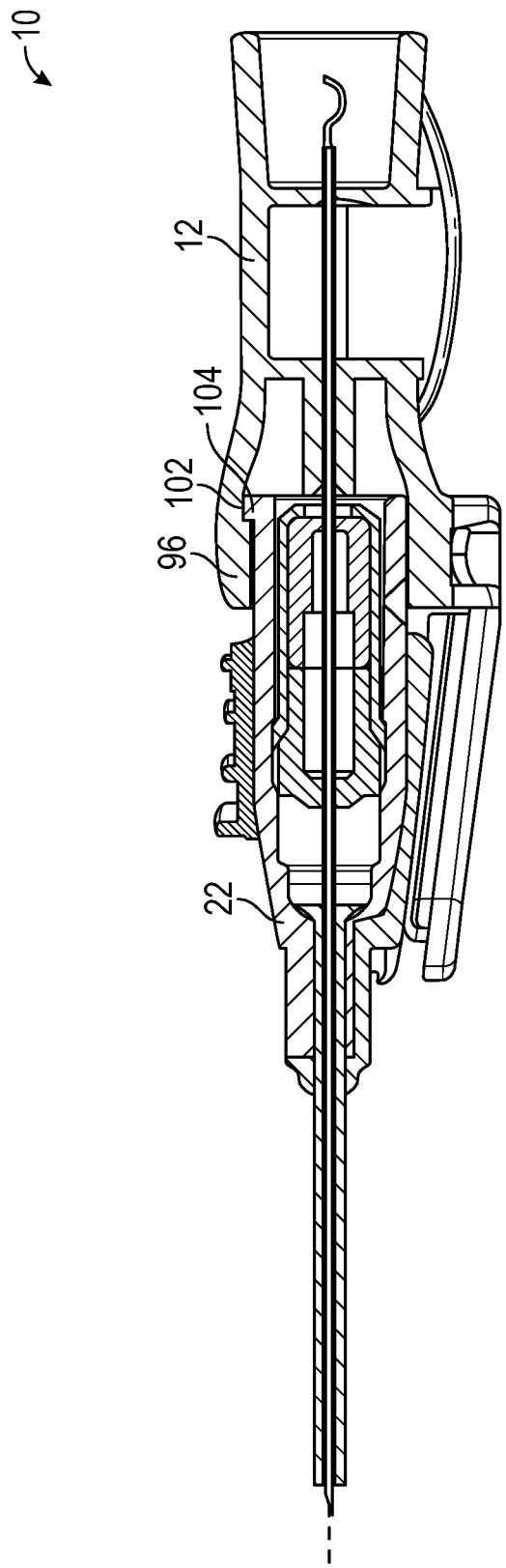
FIG. 14B is a cross-sectional view of the catheter system, illustrating the arm, according to some embodiments.

Referring now to FIGS. 14A-14B, in some embodiments, a distal end of the needle hub 12 may include an arm 96, which may include opposing edges 98a, 98b and a base 100. In some embodiments, the opposing edges 98a, 98b may extend through a wall of the needle hub 12 such that the arm 96 moves independently of a remaining portion of the needle hub 12. In some embodiments, an inner surface of the arm 96 may include a recess 102 or stepped surface, which may be configured to receive a protrusion 104 of the proximal end 32 of the catheter adapter 22 to secure the catheter adapter 22 to the needle hub 12 and prevent separation of the catheter adapter 22 and the needle hub 12. In some embodiments, the arm 96 may be flexible such that it can bend, and the arm 96 may allow the catheter adapter 22 to be removably coupled to the needle hub 12.

Figure 15A:
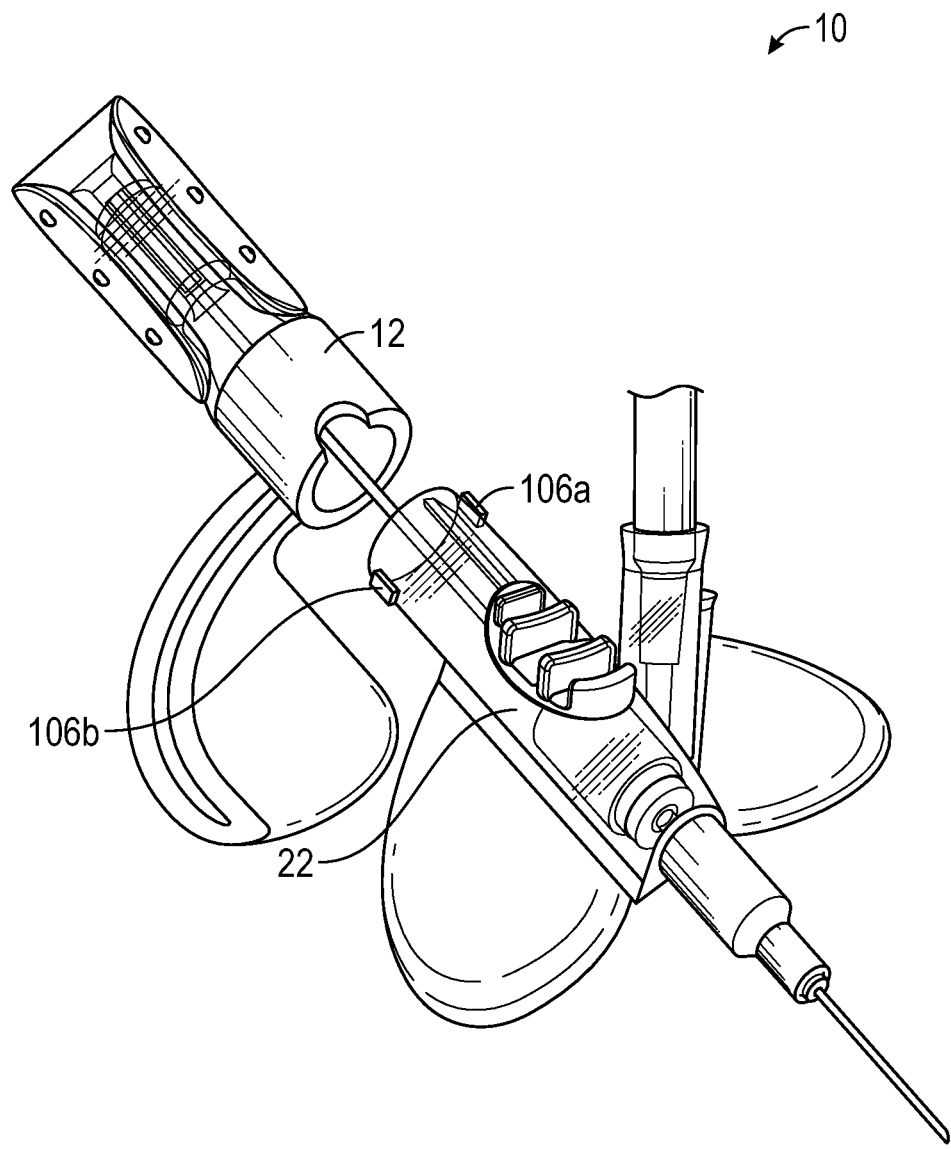
FIG. 15A is an upper perspective view of the catheter system, illustrating the needle hub removed from the catheter adapter and example protrusions to be engaged in a snap fit with the needle hub, according to some embodiments.
Figure 15B:
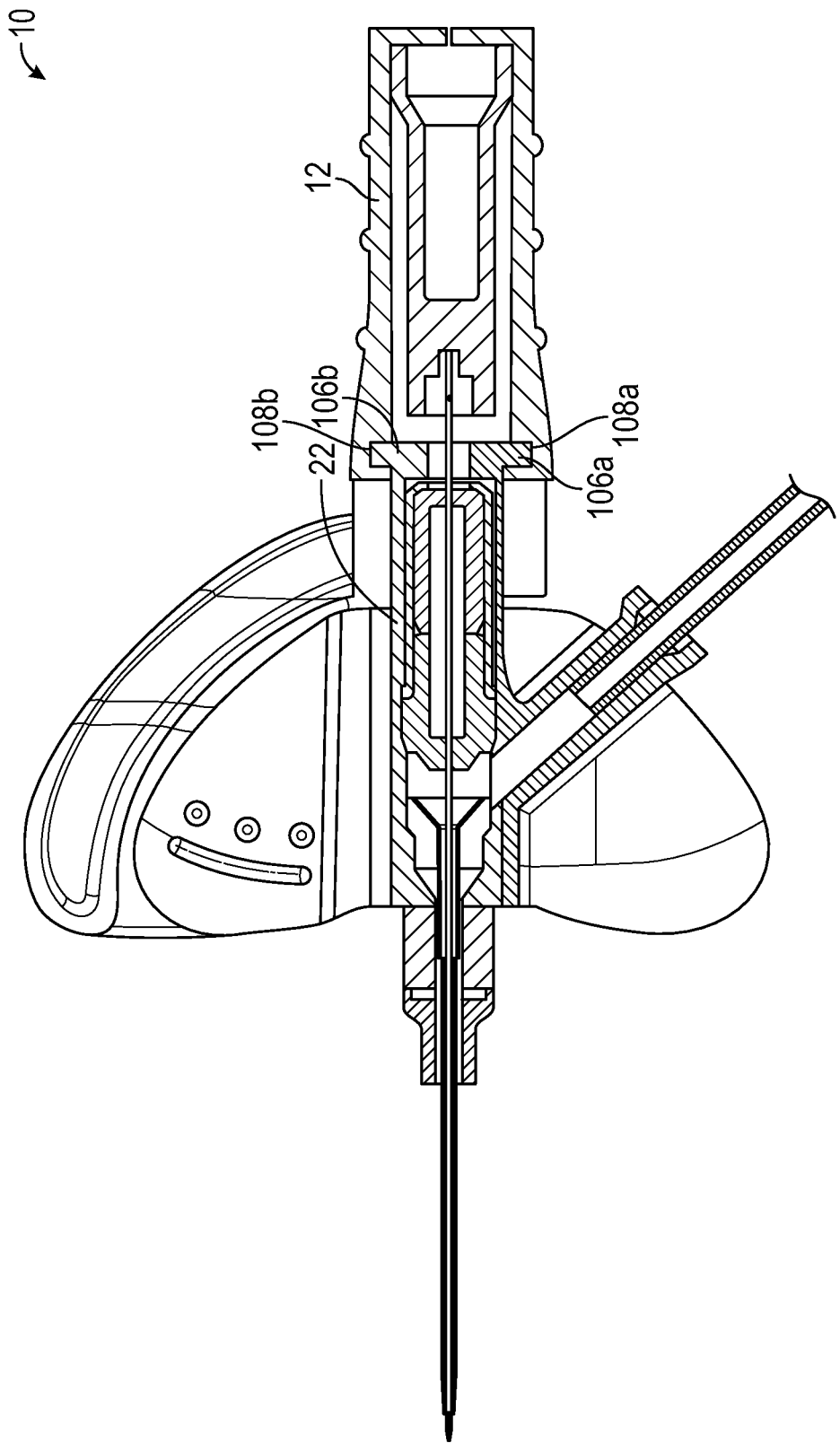
FIG. 15B is a cross-sectional view of the catheter system, illustrating the protrusions engaged in the snap fit with the needle hub, according to some embodiments.

Referring now to FIGS. 15A-15B, in some embodiments, the proximal end 32 of the catheter adapter 22 may include one or more protrusions 106a, 106b, which may be engaged in a snap fit with one or more recesses 108a, 108b of the needle hub 12. In some embodiments, the protrusions 106a, 106b may each include a ball shape, and the one or more recesses may each include a socket shape.

Figure 16:
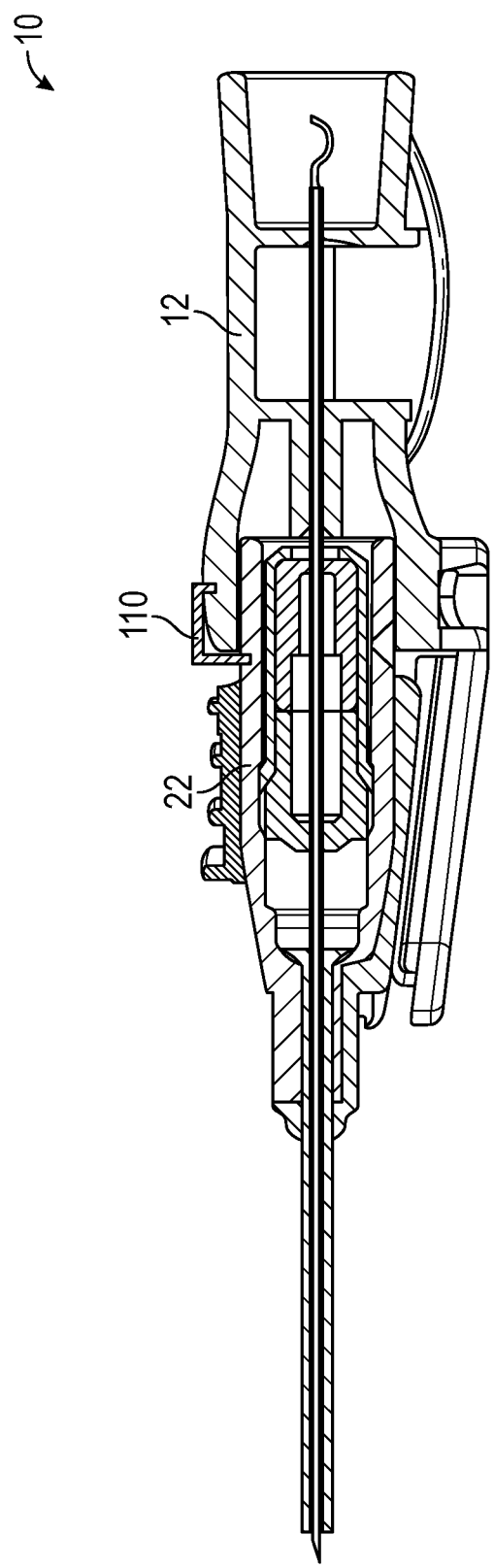
FIG. 16 is a cross-sectional view of the catheter system, illustrating an example removable clip, according to some embodiments.

Referring now to FIG. 16, in some embodiments, a removable clip 110 may be used to couple the catheter adapter 22 and the needle hub 12 together. In some embodiments, after the catheter 18 is inserted into the vasculature of the patient, the removable clip 110 may be removed to allow separation between the catheter adapter 22 and the needle hub 12. In some embodiments, the removable clip 110 may include any suitable type of clip. In some embodiments, ends of the removable clip 110 may be disposed in recesses of the catheter adapter 22 and the needle hub 12 to couple the catheter adapter 22 and the needle hub 12 together. In some embodiments, the removable clip 110 may be oriented parallel to the longitudinal axis 44. Thus, in some embodiments, only a single end of the removable clip 110 may be removed from a particular recess in which it is disposed to allow separation of the catheter adapter 22 and the needle hub 12.

Figure 17:
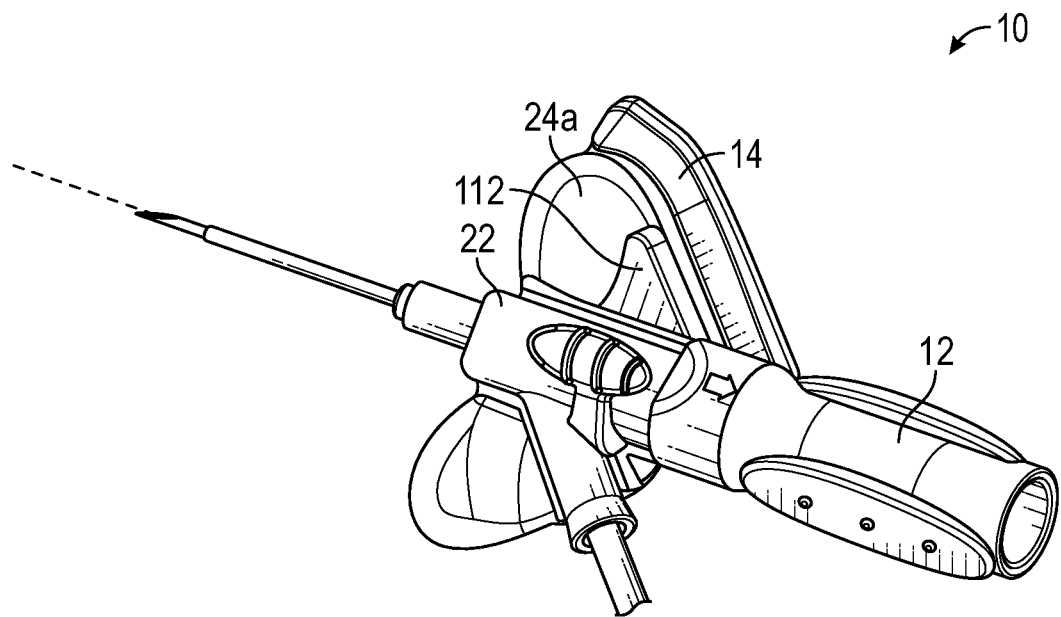
FIG. 17 is an upper perspective view of the catheter system, illustrating a raised proximal portion of the wing, according to some embodiments.

Referring now to FIG. 17, in some embodiments, the wing 24a may include a raised proximal portion 112, which may thicken the wing 24a and facilitate a better grip of the wing 24a by the user in the event the user tries to reposition the catheter adapter 22 and the needle hub 12 after they have separated.

Figure 18A:
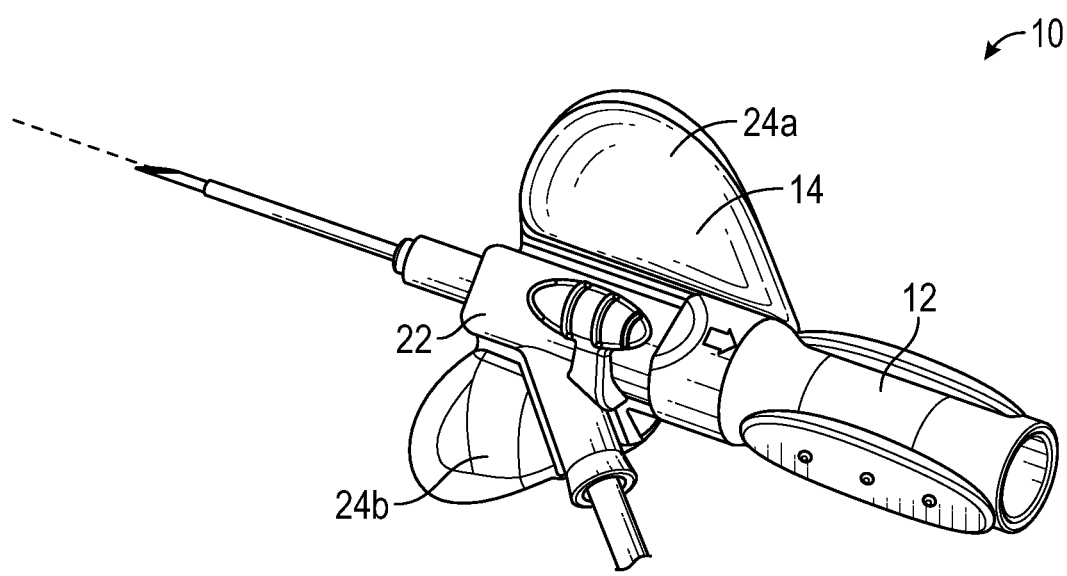
FIG. 18A is an upper perspective view of the catheter system, illustrating the paddle disposed above the wing, according to some embodiments.
Figure 18B:
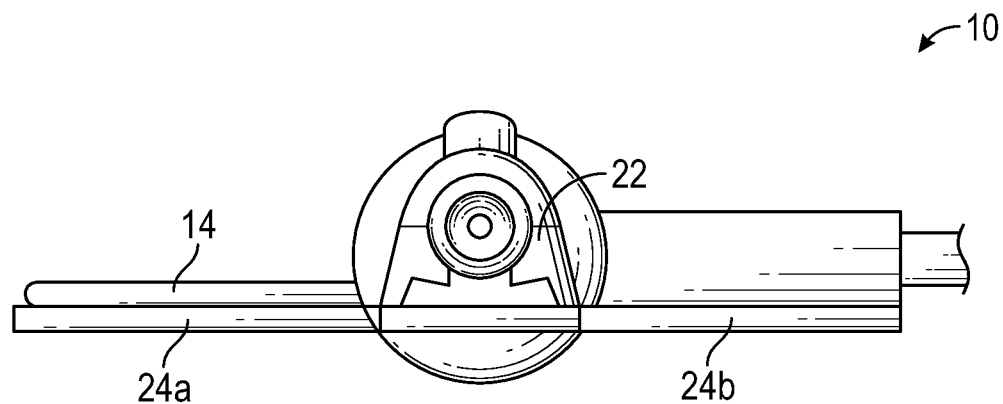
FIG. 18B is a distal end view of the catheter system, according to some embodiments.

Referring now to FIGS. 18A-18B, in some embodiments, the paddle 14 extending from a body 114 of the needle hub 12 may be disposed on top of the wing 24a. In some embodiments, when the paddle 14 is disposed on top of the wing 24a, this may prevent separation of the catheter 18 and the needle hub 12 because of a natural tendency of the user to lead with his thumb when inserting the catheter 18. In some embodiments, the thumb may be positioned on top of the paddle 14 and/or the index finger of the same hand of the user may be positioned underneath the wing 24a.

Figure 19:
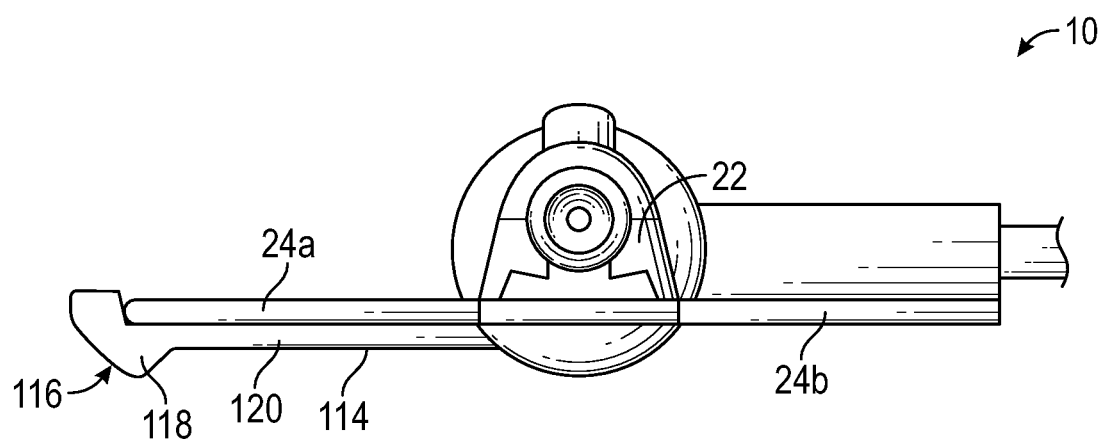
FIG. 19 is a distal end view of the catheter system, illustrating an example protrusion of the paddle, according to some embodiments.

Referring now to FIG. 19, in some embodiments, a shape of a bottom of the paddle 14 may facilitating gripping of the paddle 14 by the user. In some embodiments, an outer portion 116 of the bottom of the paddle 14 may include a protrusion 118. In some embodiments, an inner portion 120 of the bottom of the paddle 14 proximate the protrusion 118 may be generally planar. In some embodiments, the paddle 14 may be thinner at the inner portion 120 than at the outer portion 116 of the bottom of the paddle 14.

Figure 20:
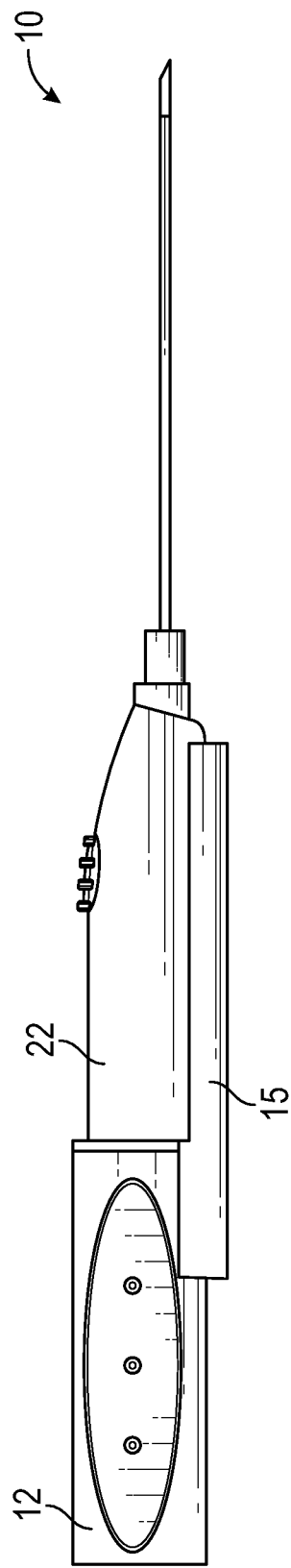
FIG. 20 is a side view of the catheter assembly, according to some embodiments.

Referring now to FIG. 20, in some embodiments, a proximal portion of the ridge 15 may be thicker than a distal portion of the ridge 15, which may facilitate gripping of the ridge 15 and the paddle 14 by the user. In some embodiments, a thickness of a distal portion of the ridge 15 may be generally uniform, which may reduce a falling forward effect in which the thumb pushes the wing 24a forward in response to contacting a taper in the distal direction. In some embodiments, the thickness of the distal portion of the ridge 15 may increase in the distal direction to reduce the falling forward effect.

Figure 21A:
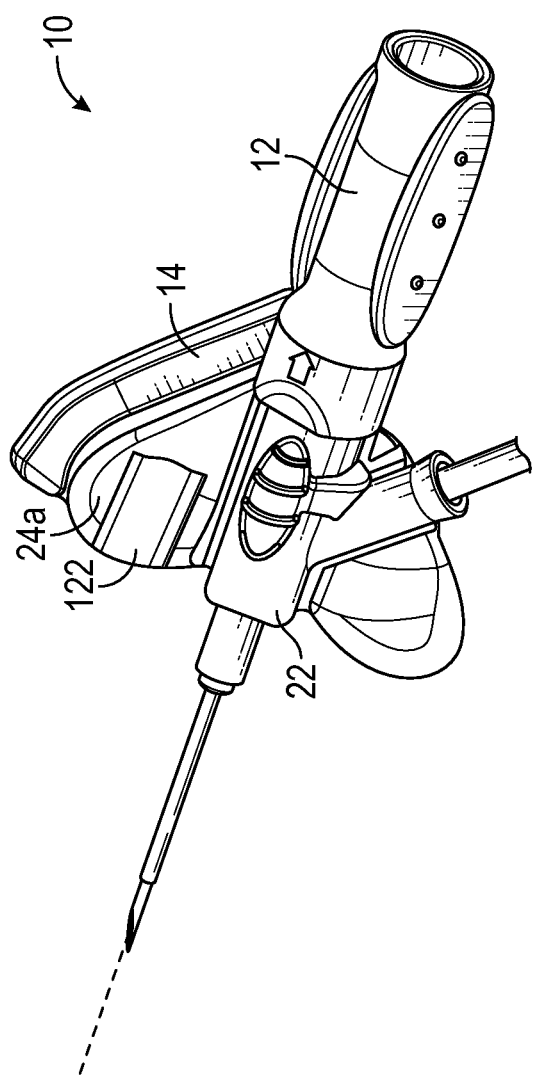
FIG. 21A is an upper perspective view of the catheter system, illustrating an example groove configured for placement of a thumb, according to some embodiments.
Figure 21B:
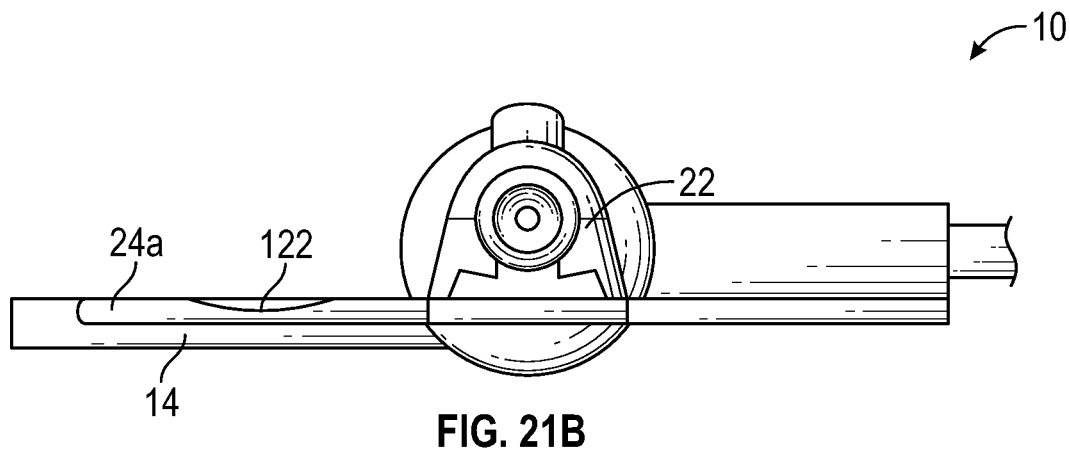
FIG. 21B is a distal end view of the catheter system, illustrating the groove, according to some embodiments.

Referring now to FIGS. 21A-21B, in some embodiments, the top of the wing 24a may include a groove 122, which may be saddle-shaped having a ridge between two higher points or peaks. In some embodiments, the groove 122 may be generally thumb-sized and configured for placement of the thumb of the user. In some embodiments, the groove 122 may be proximate a distal edge of the wing 24a, although a location of the groove 122 may vary. In some embodiments, the groove 122 may provide natural placement of the thumb so as to prevent prematurely moving the wing 24a distally from the paddle 14.

Figure 22:
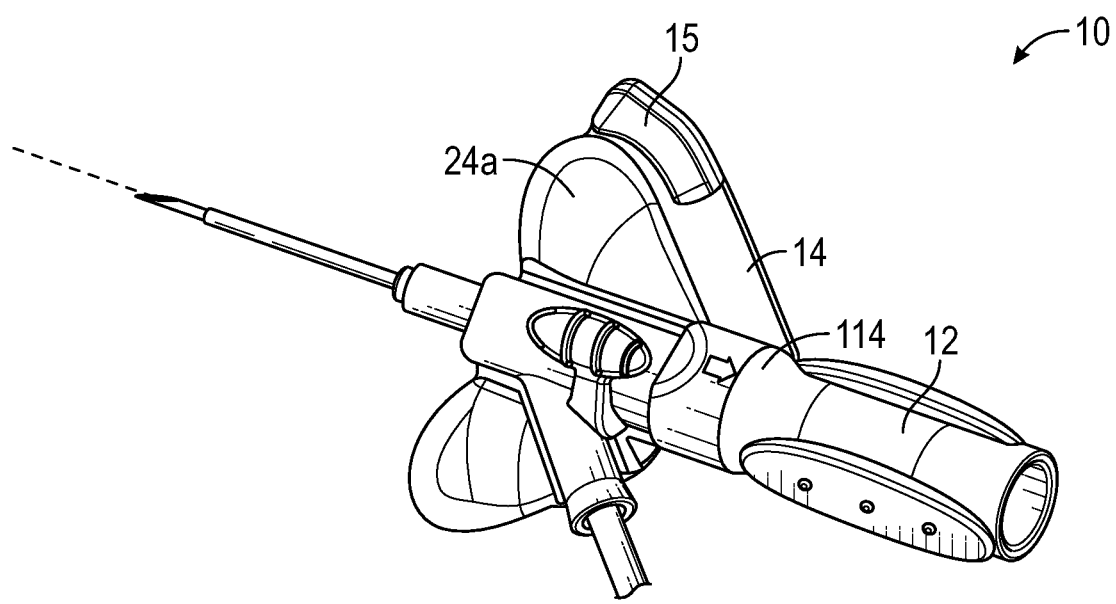
FIG. 22 is an upper perspective view of the catheter system, illustrating an example ridge, according to some embodiments.

Referring now to FIG. 22, in some embodiments, a proximal end of the ridge 15 may be removed, as illustrated, for example, in FIG. 22. Thus, in some embodiments, the ridge 15 may not extend to the body 114 of the needle hub 12. In these and other embodiments, the ridge 15 may be configured to prevent the falling forward effect described above.

Figure 23A:
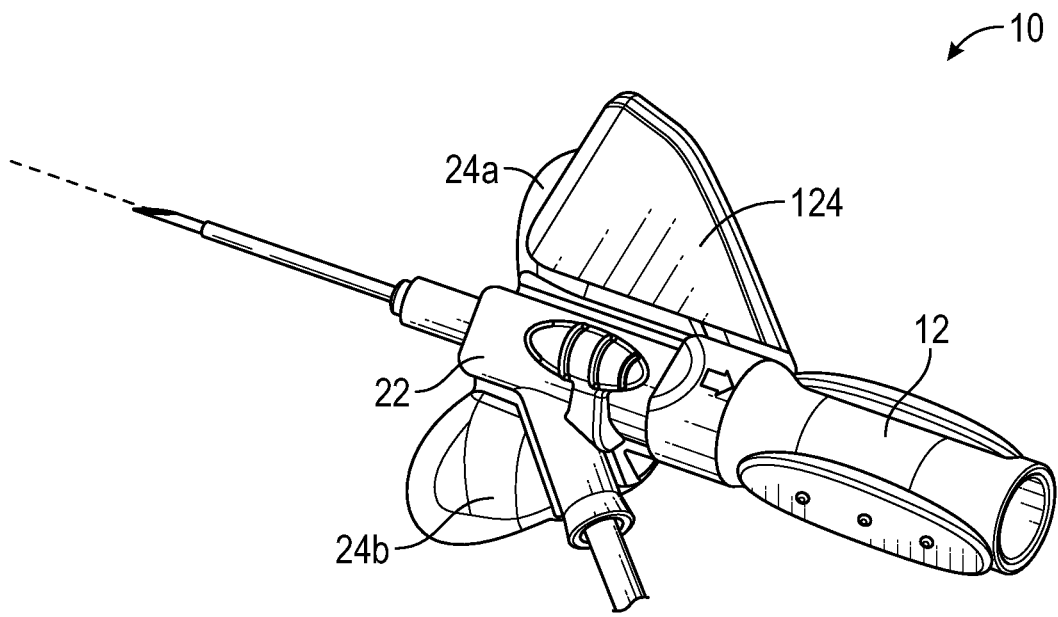
FIG. 23A is an upper perspective view of the catheter system, illustrating an example upper portion of the paddle, according to some embodiments.
Figure 23B:
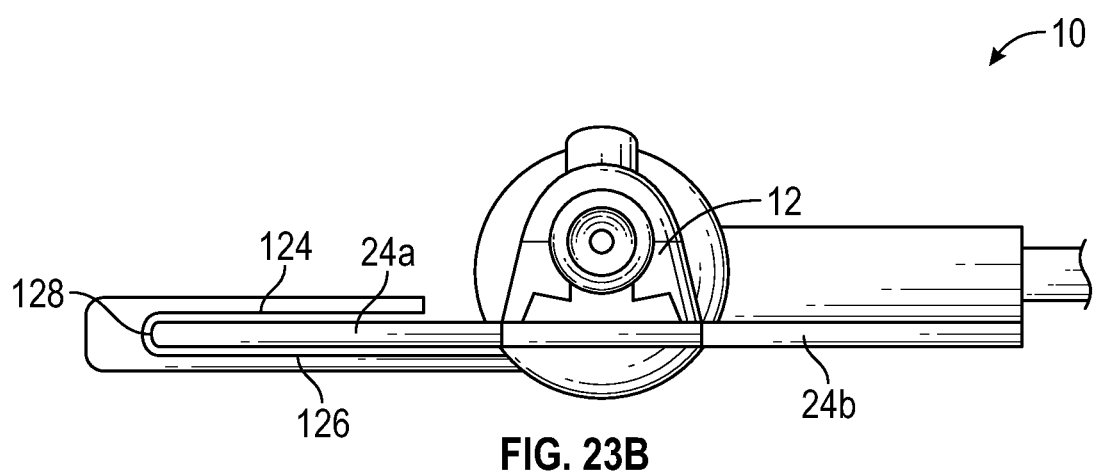
FIG. 23B is a distal end view of the catheter system, illustrating the upper portion and an example lower portion of the paddle, according to some embodiments.

Referring now to FIGS. 23A-23B, the paddle 14 may include a bend or U-shape, which may form an upper portion 124 of the paddle 14 and a lower portion 126 of the paddle 14. In some embodiments, the upper portion 124 and the lower portion 126 may be disposed above and below the wing 24a, respectively, sandwiching the wing 24a. In some embodiments, the upper portion 124 and the lower portion 126 may be spaced apart from the wing 24a, which may facilitate separation and movement between the catheter adapter 22 and the needle hub 12. In some embodiments, in response to the user pinching the upper portion 124 and the lower portion 126 together during insertion of the catheter 18, the upper portion 124 and the lower portion 126 may contact and pinch the wing 24a, thus preventing separation of the catheter adapter 22 and the needle hub 12. In some embodiments, an outer edge 128 of the wing 24a may be spaced apart from the paddle 14 before and/or after pinching by the user. In some embodiments, the upper portion 124 and/or the lower portion 126 may be constructed of a flexible material.

Figure 24A:
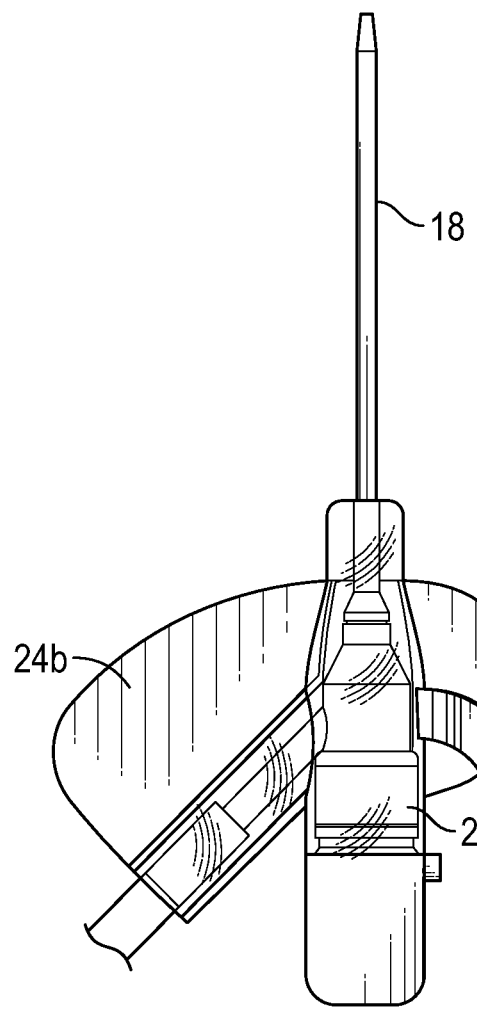
FIG. 24A is an upper perspective view of an example catheter adapter, illustrating an example other wing, according to some embodiments.
Figure 24B:
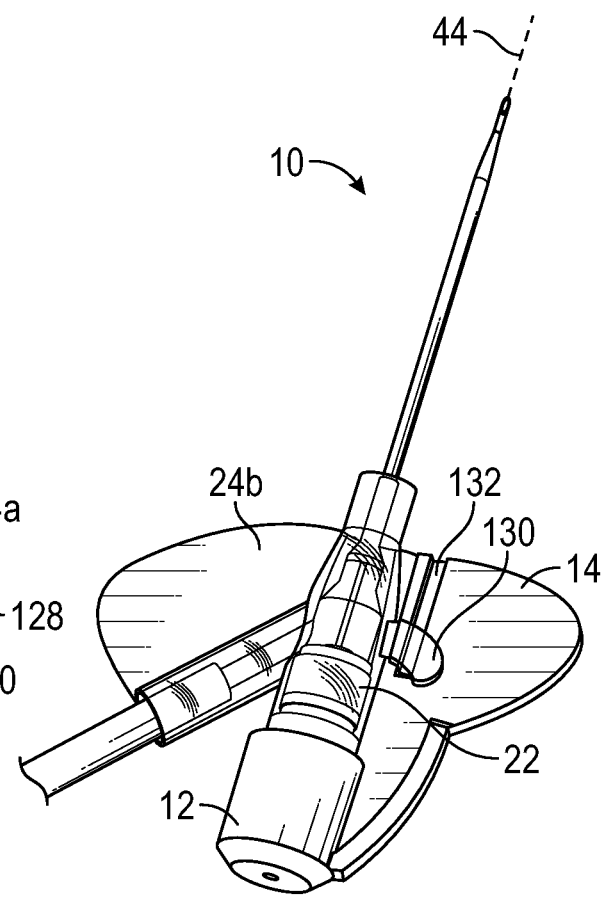
FIG. 24B is an upper perspective view of the catheter system, illustrating another example wing disposed within an example groove of the paddle and in an example down position, according to some embodiments.

Referring now to FIGS. 24A-24B, in some embodiments, the paddle 14 may be disposed on top of the wing 24a. In some embodiments, the catheter system 10 may include a wing 130, which may be smaller than the wing 24a and/or the paddle 14. In some embodiments, the wing 130 may be formed of a flexible material and may be movable between an up position and a down position. In some embodiments, the top of the paddle 14 may include a slot or groove 132.

In some embodiments, a portion of the wing 130 may be disposed within the groove 132 when the wing 130 is disposed in the down position. In some embodiments, in response to the wing 130 being disposed in the down position, the wing 130 may be configured to move along the groove 132 and prevent bending of the cannula 16 during separation of the catheter adapter 22 and the needle hub 12. In some embodiments, the groove 132 may be straight and aligned parallel to the longitudinal axis 44.

Figure 24C:
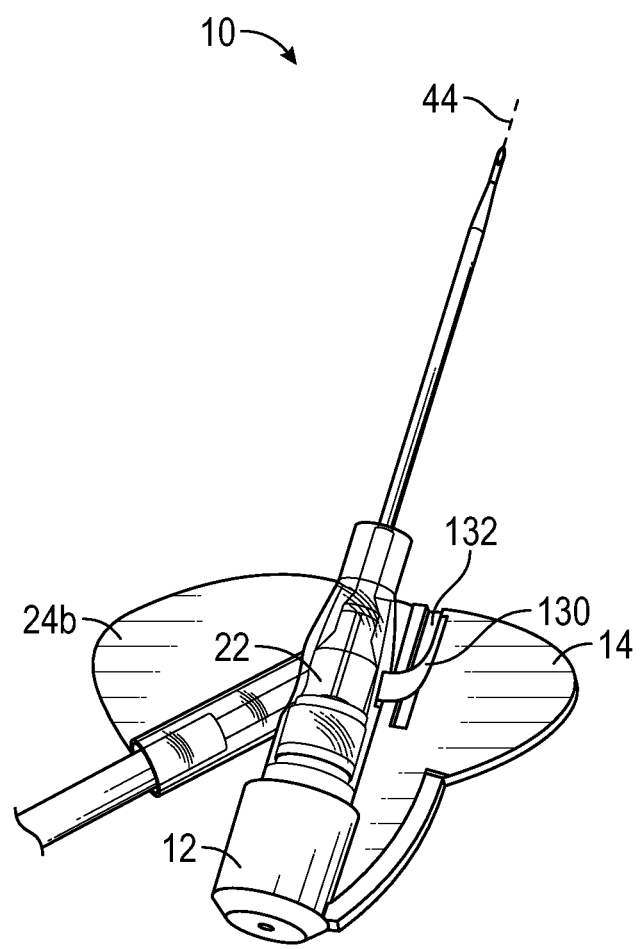
FIG. 24C is an upper perspective view of the catheter system, illustrating the other wing in an example up position, according to some embodiments.
Figure 24D:
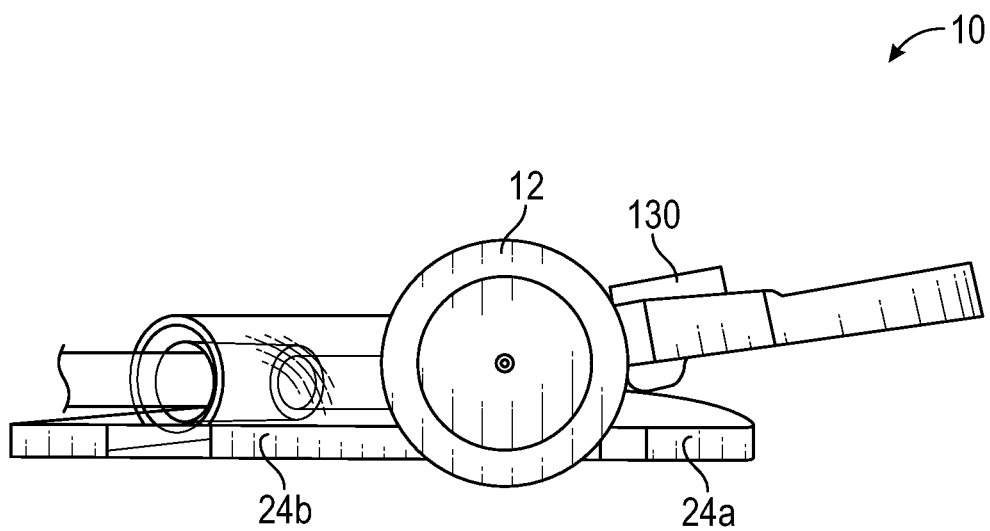
FIG. 24D is a proximal end of the catheter system, according to some embodiments.
Figure 24E:
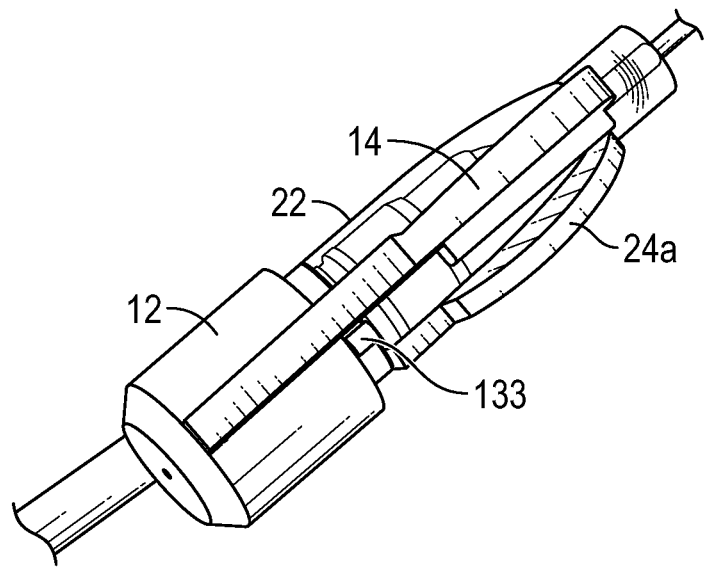
FIG. 24E is a side view of the catheter system, illustrating an example stop feature, according to some embodiments.
Figure 25A:
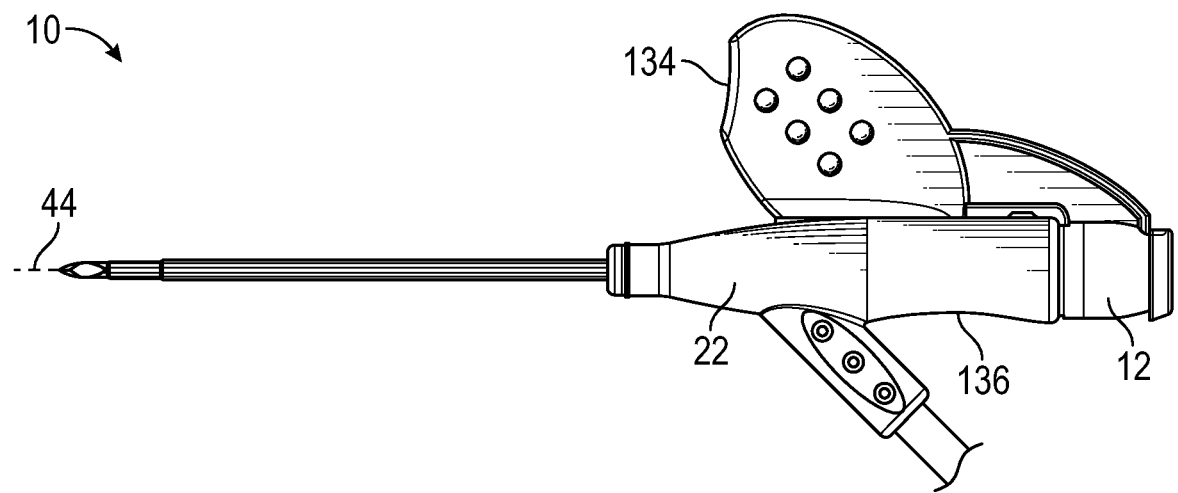
FIG. 25A is a top view of the catheter system, illustrating a plurality of concave curved surfaces, according to some embodiments.
Figure 25B:
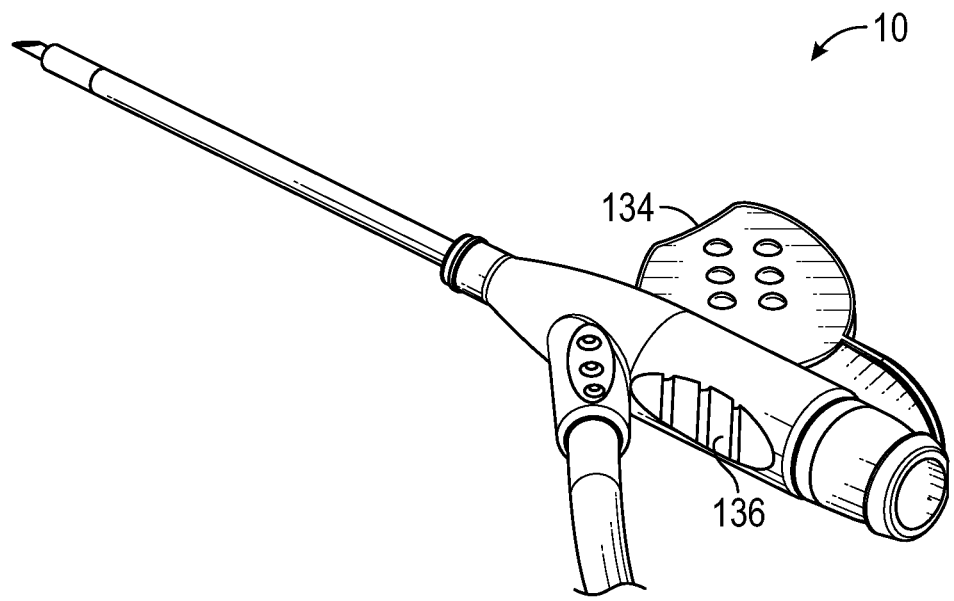
FIG. 25B is an upper perspective view of the catheter system, illustrating the concave curved surfaces, according to some embodiments.
Figure 25C:
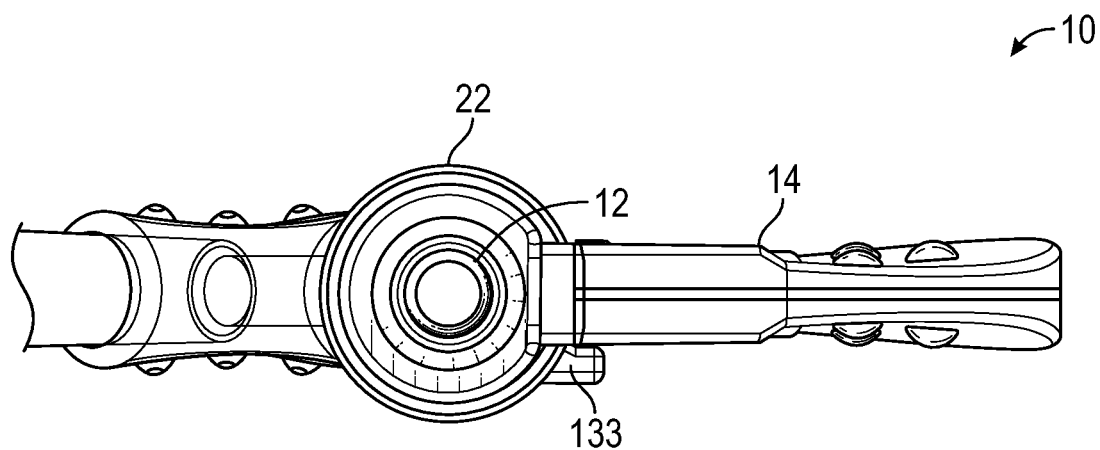
FIG. 25C is a proximal end view of the catheter system, according to some embodiments.
Figure 25D:
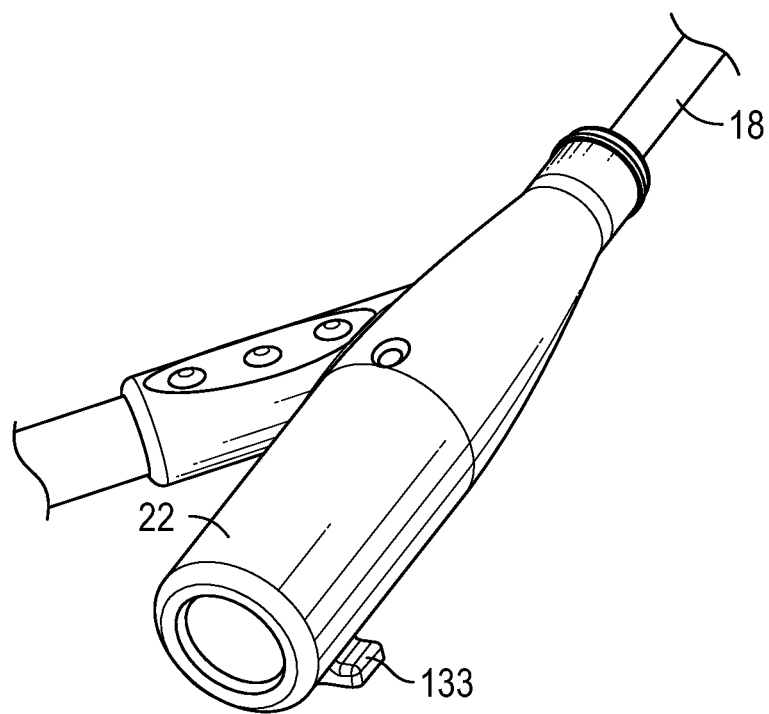
FIG. 25D is an upper perspective view of the catheter adapter, illustrating the stop feature, according to some embodiments.
Figure 25E:
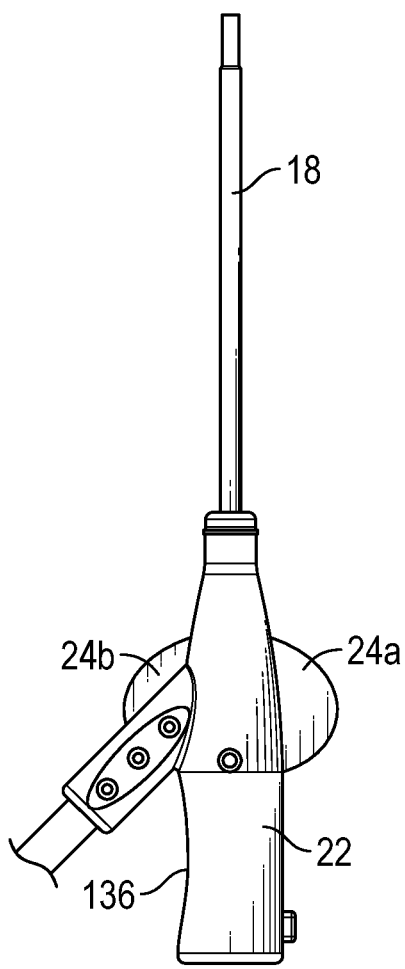
FIG. 25E is a top view of an example catheter adapter, according to some embodiments.
Figure 25F:
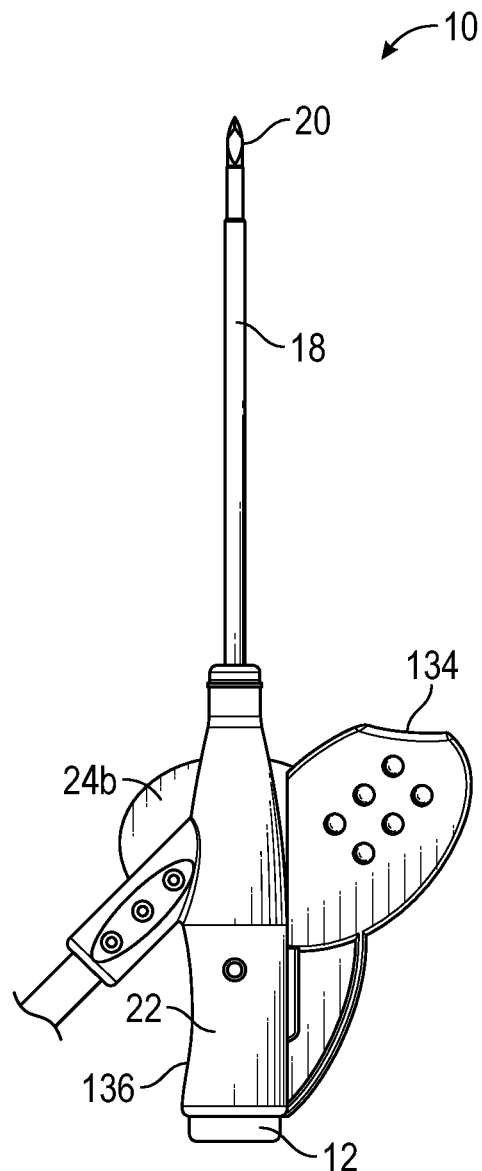
FIG. 25F is a top view of the catheter system, illustrating the concave curved surfaces, according to some embodiments.

In some embodiments, the wing 130 may extend no further than the outer edge 128 of the wing 24a. In some embodiments, the wing 130 may extend from the catheter adapter 22 or the wing 24a. FIG. 24B illustrates the wing 130 disposed in the down position, and FIG. 24C illustrates the wing 130 disposed in the up position, according to some embodiments. In some embodiments, a bottom of the wing 130 may include a protrusion or another shape that may fit within the groove 132.

In some embodiments, the wing 130 may facilitate single-hand use of the catheter system 10 and may prevent premature separation of the catheter adapter 22 and the needle hub 12. In some embodiments, the user may contact the wing 130 with his thumb and pinch the wing 130, the paddle 14, and the wing 24a between his thumb and his index finger disposed below the wing 24a. In some embodiments, the wing 130 may be moved between the down position and the up position by the thumb of the user to release the catheter adapter 22 from the needle hub 12. In some embodiments, the catheter adapter 22 may include a stop feature 133, which may be configured to contact the bottom of the paddle 14 to prevent rotation of the needle hub 12 with respect to the catheter adapter 22.

Referring now to FIGS. 25A-25F, a distal end of the paddle 14 may include a curved surface 134, which may include a concave curved surface or U-shape facing generally in the distal direction. In some embodiments, the curved surface 134 may be configured to receive the index finger of the user in a ported grip. In some embodiments, the catheter adapter 22 may include a curved surface 136 on an opposite side of the longitudinal axis 44 as the curved surface 134. In some embodiments, the curved surface 136 include a concave curved surface or U-shape that faces generally toward a side of the catheter system 10. In some embodiments, the curved surface 136 may be configured to receive the thumb of the user in the ported grip.

In some embodiments, the curved surface 136 may include one or more tactile features, which may facilitate gripping by the user. In some embodiments, the tactile features may include ribs, protrusions, grooves, bumps, etc. In some embodiments, the catheter adapter 22 may include the stop feature 133, which may be configured to contact the bottom of the paddle 14 to prevent rotation, as illustrated, for example, in FIGS. 25C-25D.

Figure 26A:
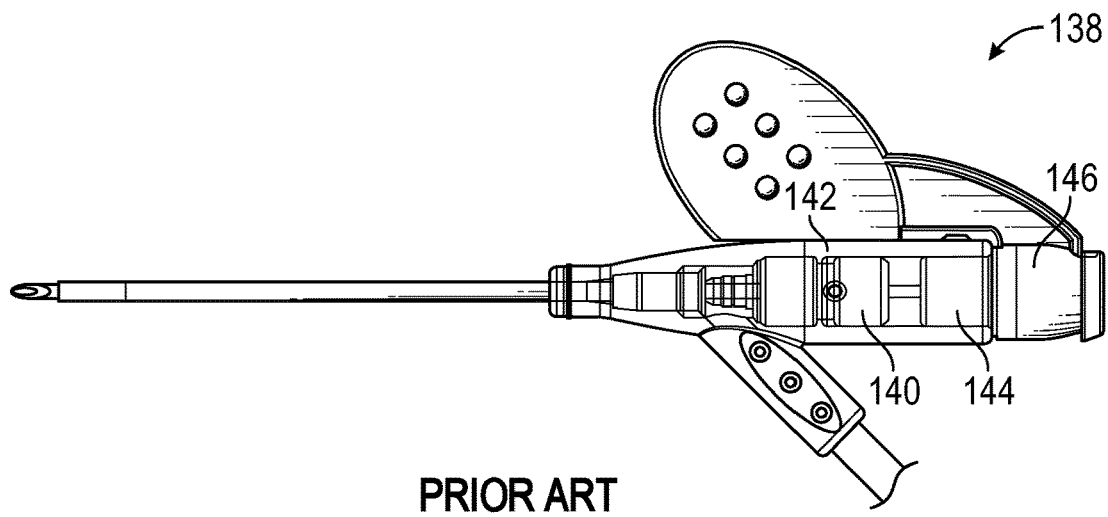
FIG. 26A is a top view of a prior art catheter system.
Figure 26B:
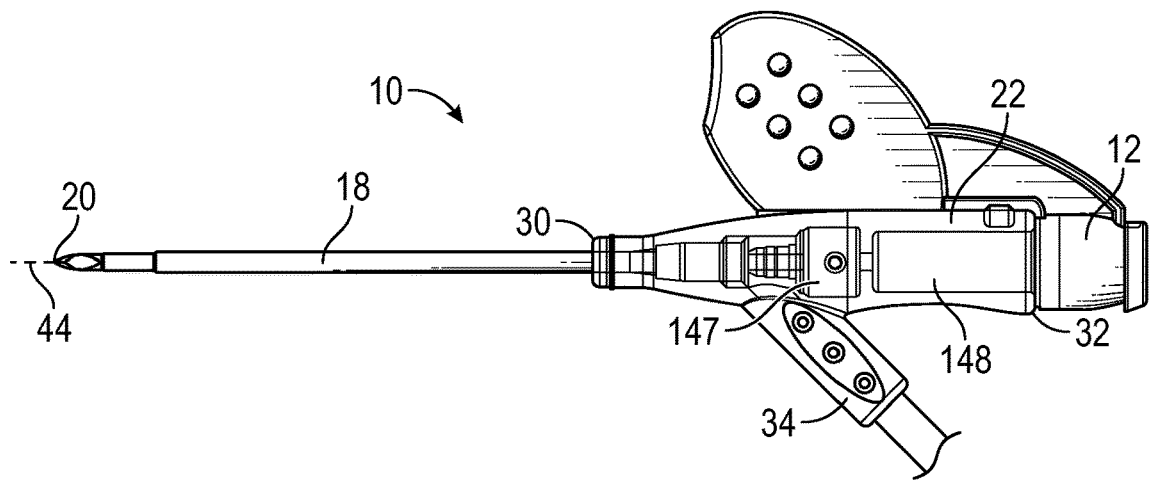
FIG. 26B is a top view of the catheter system, illustrating an elongated portion of the needle hub inserted into the catheter adapter, according to some embodiments.
Figure 26C:
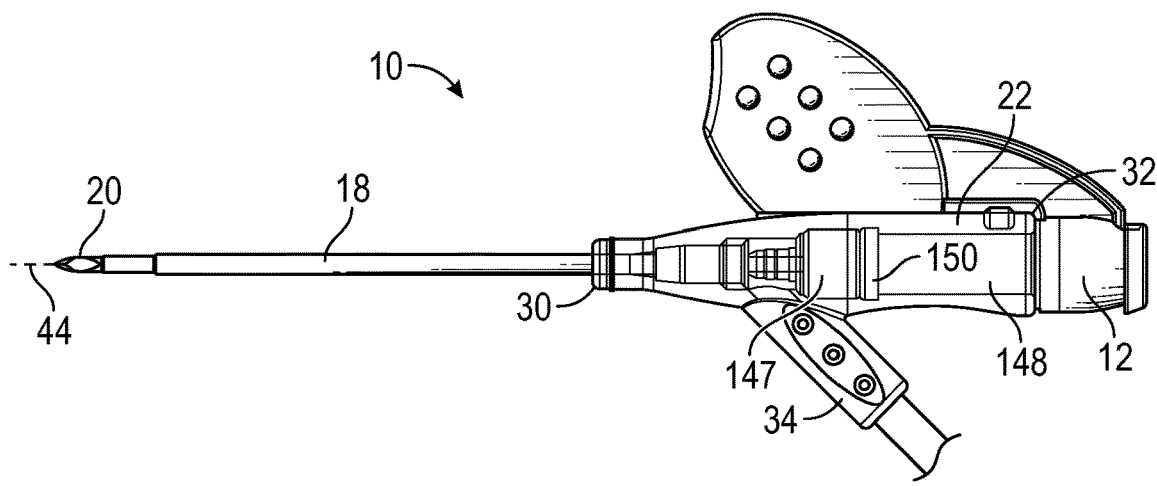
FIG. 26C is a top view of the catheter system, illustrating an example press fit washer, according to some embodiments.

Referring now to FIG. 26A, a prior art catheter system 138 is illustrated. The prior art catheter system 138 may include a septum 140 disposed within a catheter adapter 142 and a portion 144 of a needle hub 146 may be inserted into the catheter adapter 142. Referring now to FIGS. 26B-26C, the catheter system 10 may include a septum 147 that is shorter than the septum 140 of the prior art catheter system 138. In some embodiments, a portion 148 of the needle hub 12 that is inserted into the catheter adapter 22 when the catheter adapter 22 and the needle hub 12 are coupled together may be longer than the portion 144, facilitating greater stability and enhanced alignment between the catheter adapter 22 and the needle hub 12 during insertion of the catheter 18 into the vasculature. In some embodiments, the catheter adapter 22 may include a low-drag septum; for example, the septum 147 may be low-drag.

In some embodiments, a distal end of the septum 147 may be near or proximate a junction of a lumen of the side port 34 with the lumen of the catheter adapter 22 that extends between the distal end 30 and the proximal end 32 of the catheter adapter 22. In some embodiments, a proximal end of the septum 147 may be distal to a proximal end of the side port 34. In some embodiments, a press fit washer 150 may be disposed between the portion 148 and the septum 147, which may allow the catheter system 10 to withstand high pressures.

Figure 26D:
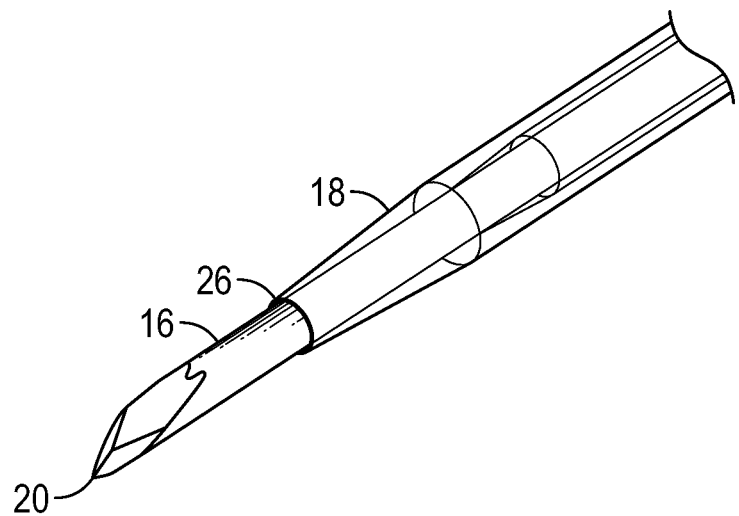
FIG. 26D is an upper perspective view of an example distal end of the catheter system, illustrating an example solid cannula, according to some embodiments.
Figure 26E:
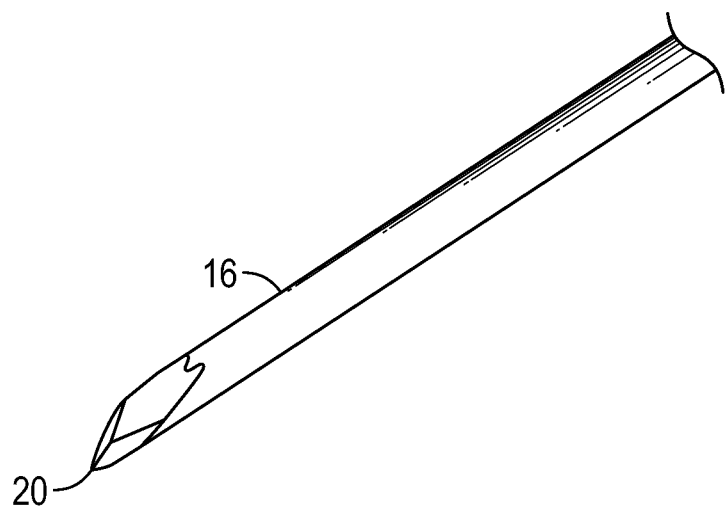
FIG. 26E is an upper perspective view of the cannula, according to some embodiments.

Referring now to FIGS. 26D-26E, in some embodiments, the cannula 16 may include a solid introducer needle, which may not include any notches. In some embodiments, the solid introducer needle may reduce a length of the septum 147 and/or increase a length of the portion 148. In some embodiments, the solid introducer needle may be constructed via extrusion, grinding, laser, etching, or another suitable method.

Figure 27A:
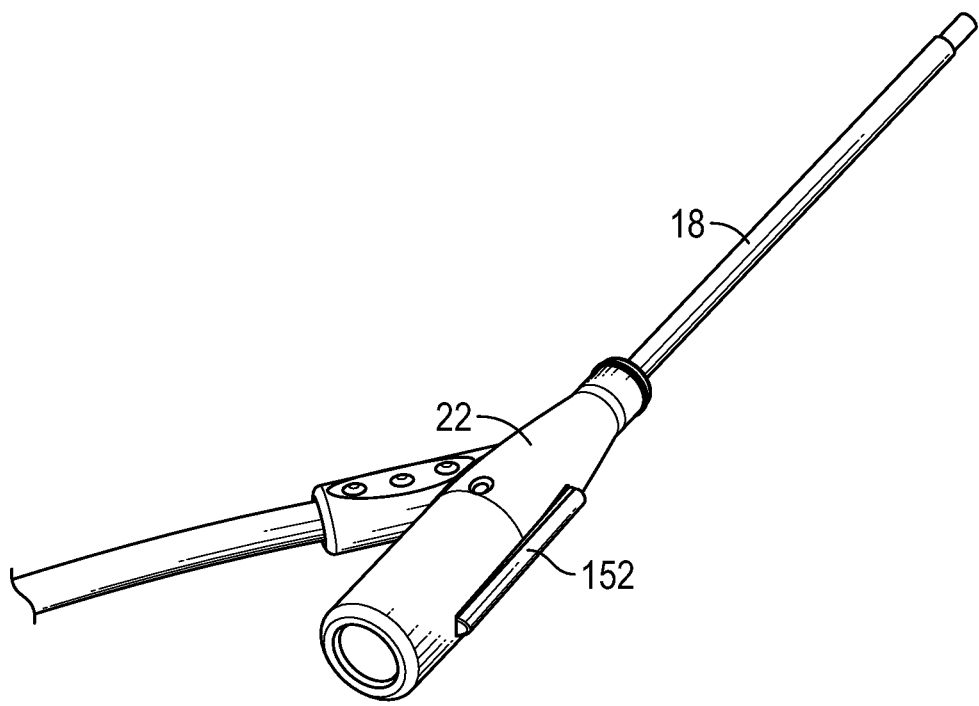
FIG. 27A is an upper perspective view of the catheter adapter, illustrating an example rib, according to some embodiments.
Figure 27B:
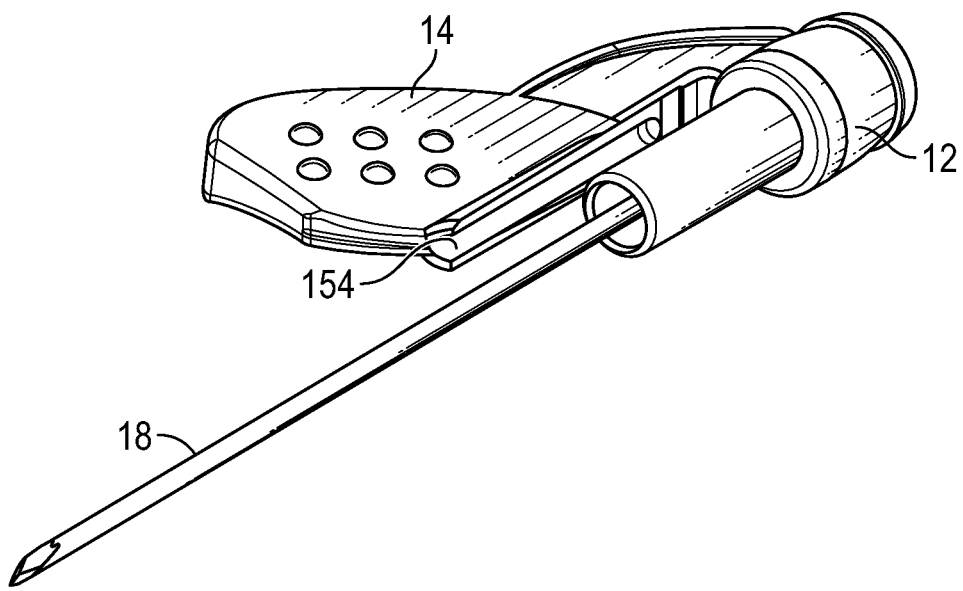
FIG. 27B is an upper perspective view of the needle hub, illustrating an example groove configured to receive the rib, according to some embodiments.
Figure 27C:
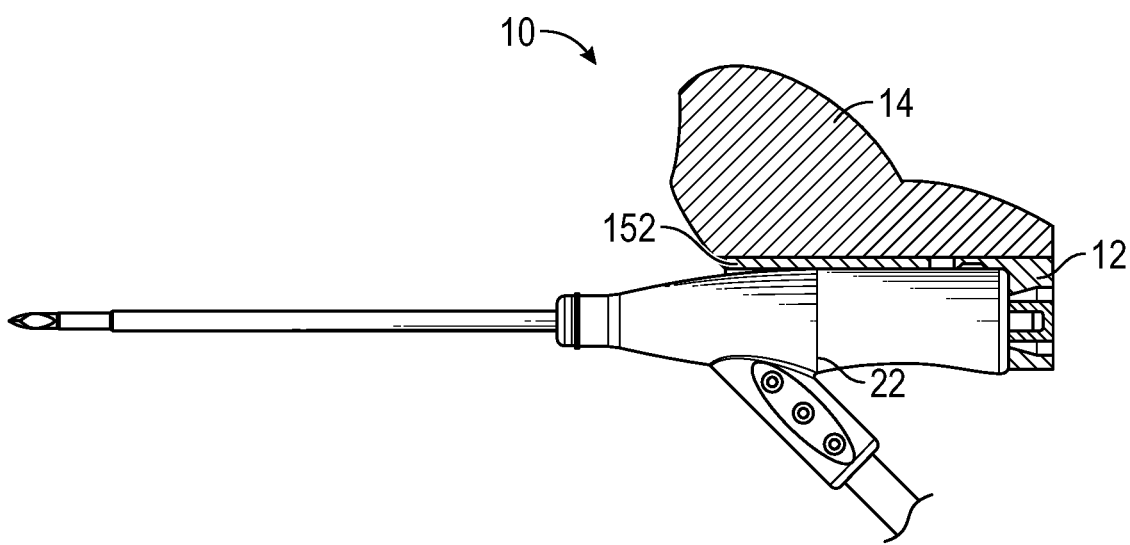
FIG. 27C is a cutaway view of the catheter system, illustrating the rib disposed within the groove, according to some embodiments.

Referring now to FIGS. 27A-27C, in some embodiments, the catheter adapter 22 may include a rib 152, which may be generally aligned with the longitudinal axis 44. In some embodiments, an inner portion of the paddle 14 may include a groove 154, which may also be generally aligned with the longitudinal axis 44. In some embodiments, the rib 152 may be disposed within the groove 154, which may facilitate alignment of the catheter adapter 22 and the needle hub 12 during insertion of the catheter 18 into the vasculature of the patient and/or withdrawal of the cannula 16 from the catheter adapter 22. In some embodiments, the cannula 16 may include a solid introducer needle or a lumen extending there through. In some embodiments, the user may push and pull the paddle 14 with respect to the catheter adapter 22 in order to overcome any friction resisting movement of the rib 152 with respect to the groove 154.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention. It should be understood that the embodiments may be combined.

We claim:

1. A catheter system comprising:
a needle hub;
a needle that extends distally from the needle hub;
a paddle that extends outwardly and distally from the needle hub, the paddle including a ridge that extends upwardly along a proximal edge and an outer edge of the paddle, an upper surface of the paddle including a flat and smooth paddle portion that extends between the ridge and an inner edge and a distal edge of the paddle;
a catheter adapter that selectively couples with the needle hub;
a catheter that extends distally from the catheter adapter; and
a wing that extends outwardly from the catheter adapter, the wing including a proximal edge and an outer edge that conform to the ridge to thereby cause the wing to abut the ridge when the catheter adapter is coupled with the needle hub, the wing including a distal edge positioned beyond the distal edge of the paddle when the proximal edge and the outer edge of the wing abut the ridge to thereby form a distal wing portion that is positioned beyond the distal edge of the paddle, a lower surface of the wing including a flat and smooth wing portion that extends between the proximal edge and the outer edge of the wing to the catheter adapter;
wherein the wing further includes a socket at a first position within the flat and smooth wing portion and the paddle further includes a ball at a second position within the flat and smooth paddle portion, the first position aligning with the second position when the proximal edge and the outer edge of the wing abut the ridge, the ball having a diameter that matches a diameter of the socket to thereby cause the ball to insert into and be snugly held within the socket when the flat and smooth wing portion is positioned against the flat and smooth paddle portion and the proximal edge and the outer edge of the wing abut the ridge;
wherein the paddle is formed of a rigid material and the wing is formed of a flexible material such that, when a user grasps the distal wing portion and applies a lifting force to the distal wing portion relative to the paddle, the wing flexes upwardly away from the paddle without deflecting the paddle to thereby remove the socket from the ball without moving the needle hub proximally relative to the catheter adapter; and
wherein the ridge does not extend to the needle hub.

2. The catheter system of claim 1, wherein the distal edge of the paddle includes a concave curved surface that is positioned below the distal wing portion when the proximal edge and the outer edge of the wing abut the ridge.

3. The catheter system of claim 1, wherein the needle hub includes a second concave curved surface that is oriented away from the paddle.

4. The catheter system of claim 1, wherein the paddle includes a protrusion that extends downwardly along the outer edge of the paddle.

5. The catheter system of claim 1, wherein a proximal portion of the ridge is thicker than a distal portion of the ridge.

6. The catheter system of claim 5, wherein the thickness of the distal portion of the ridge is uniform.

7. The catheter system of claim 5, wherein the thickness of the distal portion of the ridge increases in a distal direction.

8. A catheter system comprising:
a needle hub;
a needle that extends distally from the needle hub;
a paddle that extends outwardly and distally from the needle hub, the paddle including a ridge that extends upwardly along a proximal edge and an outer edge of the paddle, a proximal portion of the ridge being thicker than a distal portion of the ridge and a thickness of the distal portion of the ridge being uniform, the paddle also including a protrusion that extends downwardly along the outer edge of the paddle, an upper surface of the paddle including a flat and smooth paddle portion that extends between the ridge and an inner edge and a distal edge of the paddle;
a catheter adapter that selectively couples with the needle hub;
a catheter that extends distally from the catheter adapter; and
a wing that extends outwardly from the catheter adapter, the wing including a proximal edge and an outer edge that conform to the ridge to thereby cause the wing to abut the ridge when the catheter adapter is coupled with the needle hub, the wing including a distal edge positioned beyond the distal edge of the paddle when the proximal edge and the outer edge of the wing abut the ridge to thereby form a distal wing portion that is positioned beyond the distal edge of the paddle, a lower surface of the wing including a flat and smooth wing portion that extends between the proximal edge and the outer edge of the wing to the catheter adapter;
wherein the wing further includes a socket at a first position within the flat and smooth wing portion and the paddle further includes a ball at a second position within the flat and smooth paddle portion, the first position aligning with the second position when the proximal edge and the outer edge of the wing abut the ridge, the ball having a diameter that matches a diameter of the socket to thereby cause the ball to insert into and be snugly held within the socket when the flat and smooth wing portion is positioned against the flat and smooth paddle portion and the proximal edge and the outer edge of the wing abut the ridge;

wherein the paddle is formed of a rigid material and the wing is formed of a flexible material such that, when a user grasps the distal wing portion and applies a lifting force to the distal wing portion relative to the paddle, the wing flexes upwardly away from the paddle without deflecting the paddle to thereby remove the socket from the ball without moving the needle hub proximally relative to the catheter adapter;

wherein the distal edge of the paddle includes a concave curved surface that is positioned below the distal wing portion when the proximal edge and the outer edge of the wing abut the ridge and the needle hub includes a second concave curved surface that is oriented away from the paddle;

wherein the ridge does not extend to the needle hub.

* * * * *